(12) United States Patent
Elliott

(10) Patent No.: US 9,795,389 B2
(45) Date of Patent: Oct. 24, 2017

(54) EMBOLIC COILS AND RELATED COMPONENTS, SYSTEMS, AND METHODS

(71) Applicant: Boston Scientific Scimed Inc., Maple Grove, MN (US)

(72) Inventor: Christopher J. Elliott, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 482 days.

(21) Appl. No.: 14/068,509

(22) Filed: Oct. 31, 2013

(65) Prior Publication Data

US 2014/0081313 A1 Mar. 20, 2014

Related U.S. Application Data

(63) Continuation of application No. 11/425,546, filed on Jun. 21, 2006, now abandoned.

(51) Int. Cl.
  *A61B 17/12* (2006.01)
  *A61B 17/00* (2006.01)
  *A61B 90/00* (2016.01)

(52) U.S. Cl.
  CPC ...... *A61B 17/1214* (2013.01); *A61B 17/1215* (2013.01); *A61B 17/12022* (2013.01); *A61B 17/12113* (2013.01); *A61B 17/12145* (2013.01); *A61B 17/12131* (2013.01); *A61B 90/37* (2016.02); *A61B 90/39* (2016.02); *A61B 2017/00004* (2013.01); *A61B 2017/00526* (2013.01); *A61B 2017/00867* (2013.01); *A61B 2017/12054* (2013.01)

(58) Field of Classification Search
  CPC .................................... A61B 17/12131
  USPC .......................................... 606/200
  See application file for complete search history.

(56) References Cited

U.S. PATENT DOCUMENTS

| | | | | |
|---|---|---|---|---|
| 5,217,484 A | * | 6/1993 | Marks | 606/200 |
| 6,277,125 B1 | * | 8/2001 | Barry et al. | 606/108 |
| 6,958,074 B2 | * | 10/2005 | Russell | 606/200 |
| 7,201,768 B2 | * | 4/2007 | Diaz et al. | 623/1.11 |
| 7,942,894 B2 | * | 5/2011 | West | 606/200 |
| 2003/0212429 A1 | * | 11/2003 | Keegan et al. | 606/200 |
| 2006/0184193 A1 | * | 8/2006 | Lowe et al. | 606/200 |

* cited by examiner

*Primary Examiner* — Diane Yabut

(57) ABSTRACT

The present invention relates generally to systems and methods for delivering embolic devices into a body lumen of a patient. These embolic devices are applicable to a variety of neurological and/or peripheral applications. In particular, the embolic devices may be used to occlude a vessel within a patient, and/or to treat aneurysms, arteriovenous malformations, traumatic fistulas, uterine fibroids or cancer.

12 Claims, 18 Drawing Sheets

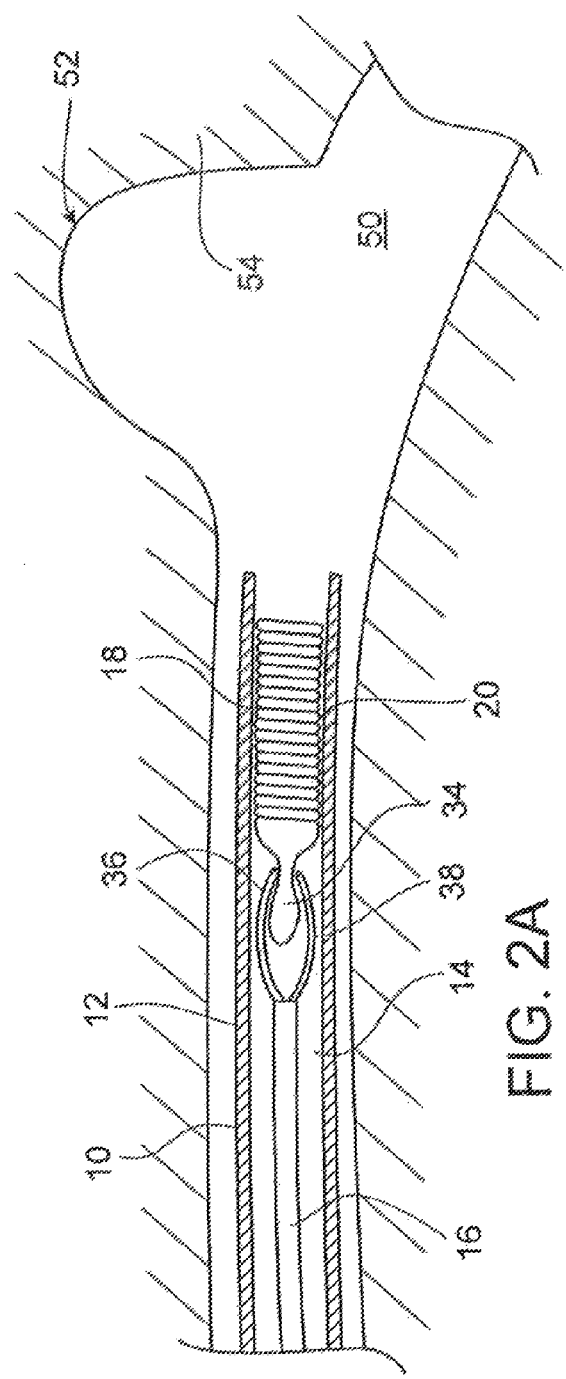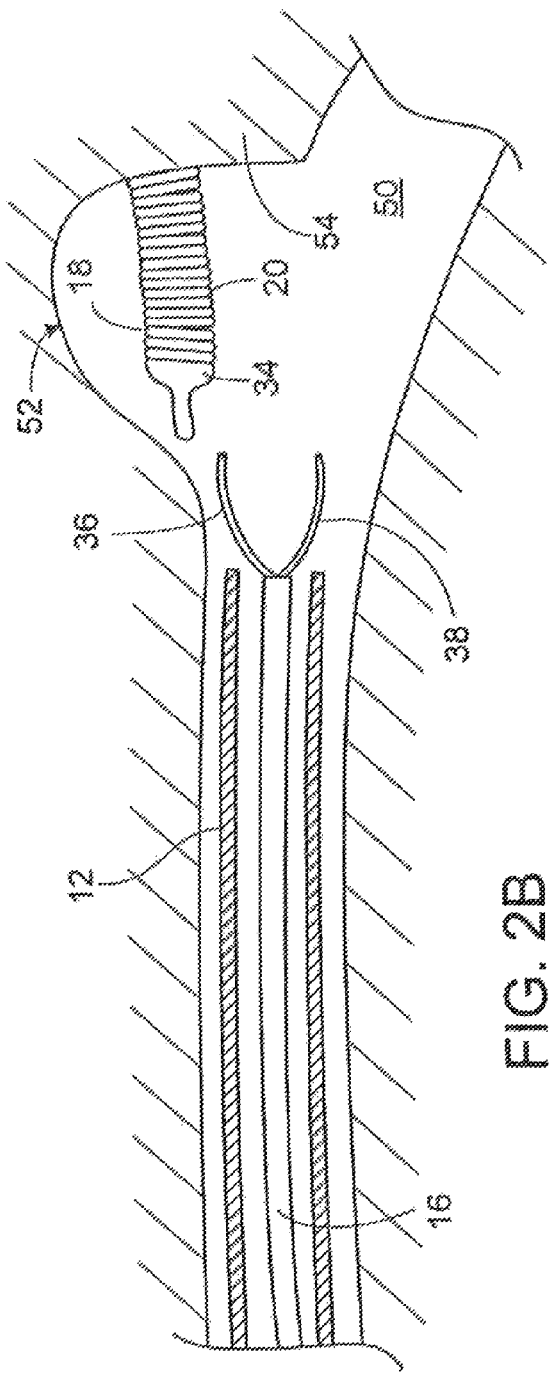

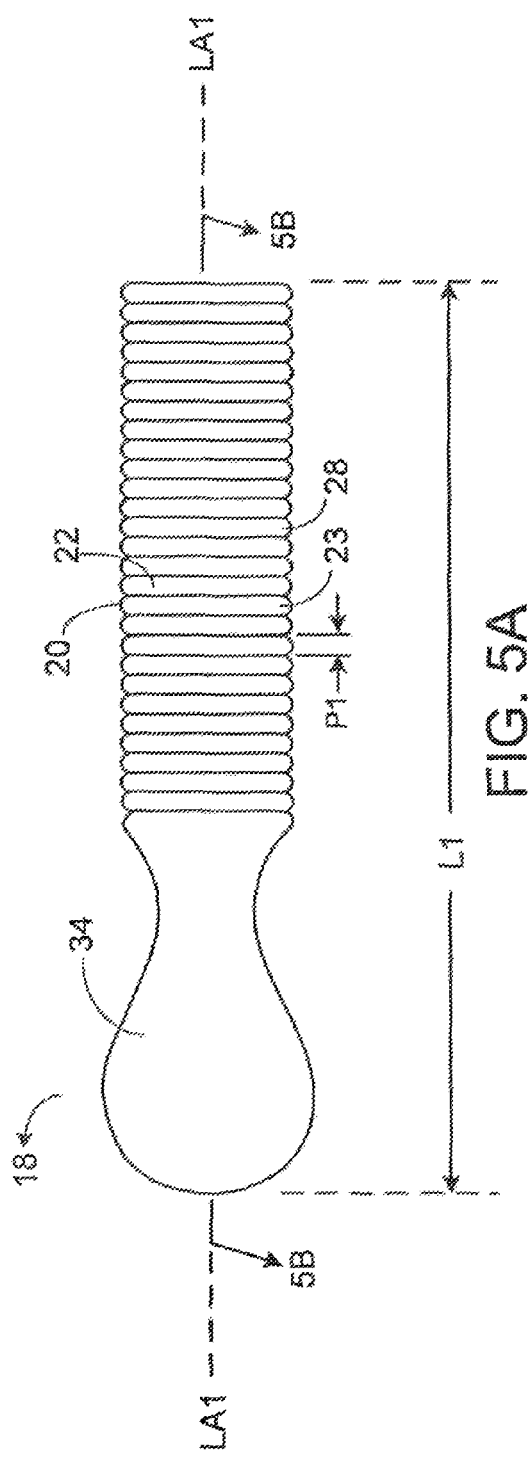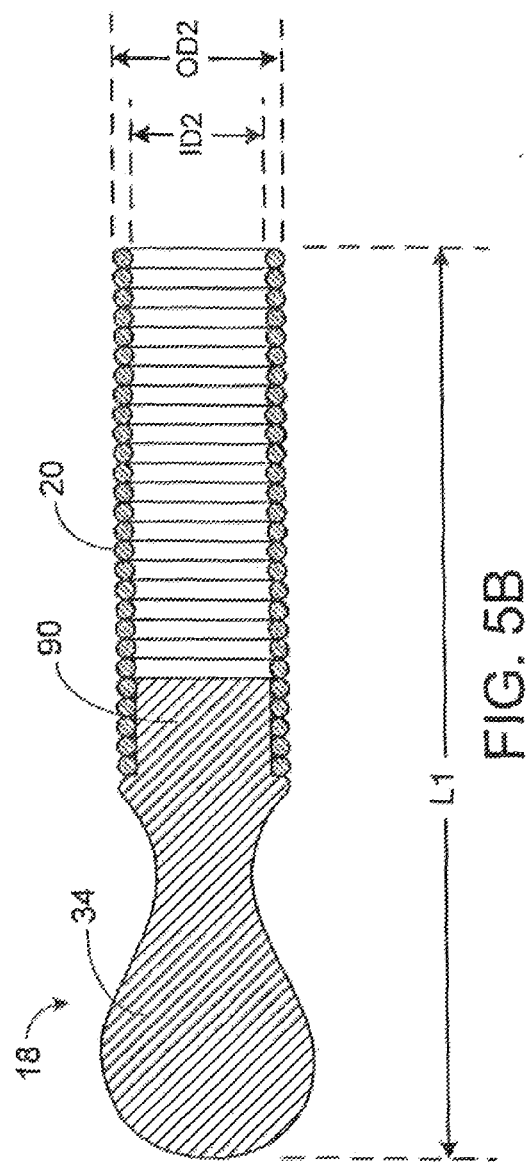

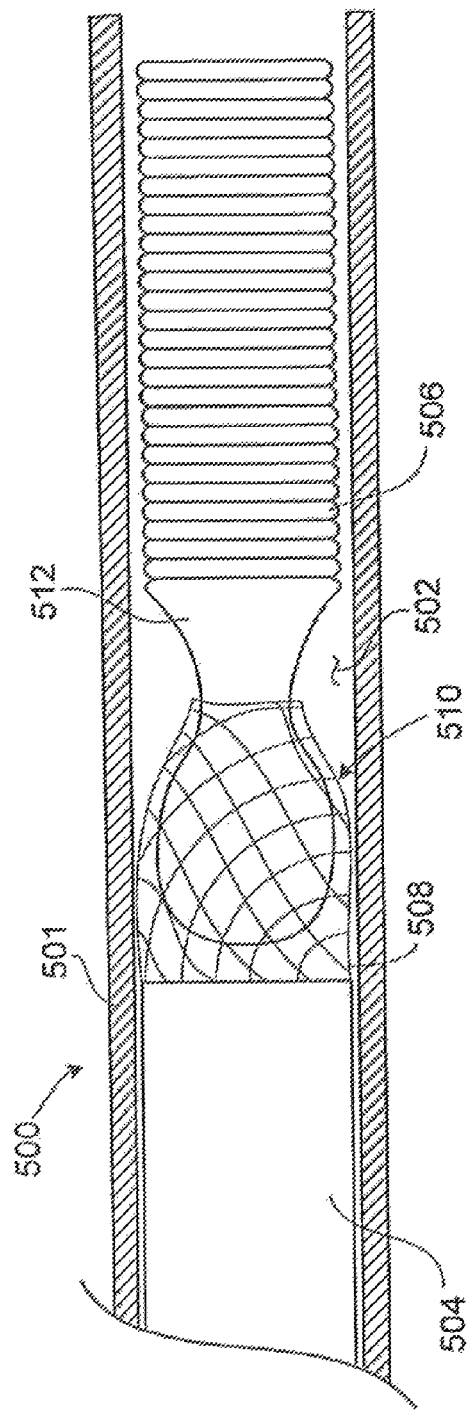
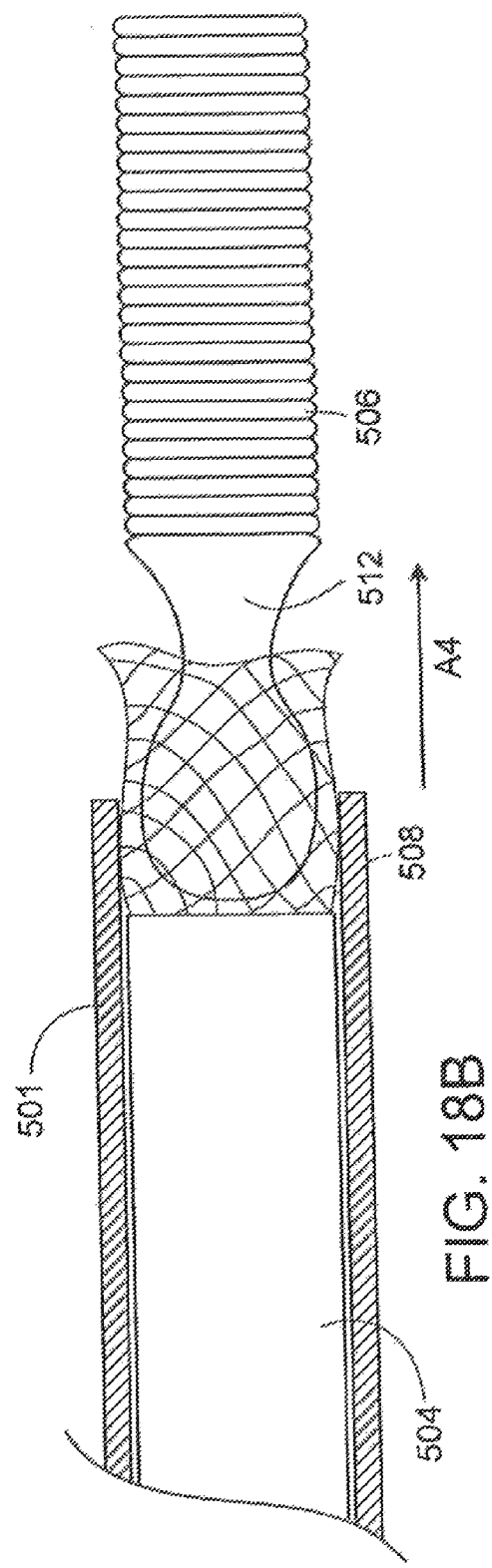
FIG. 18A
FIG. 18B

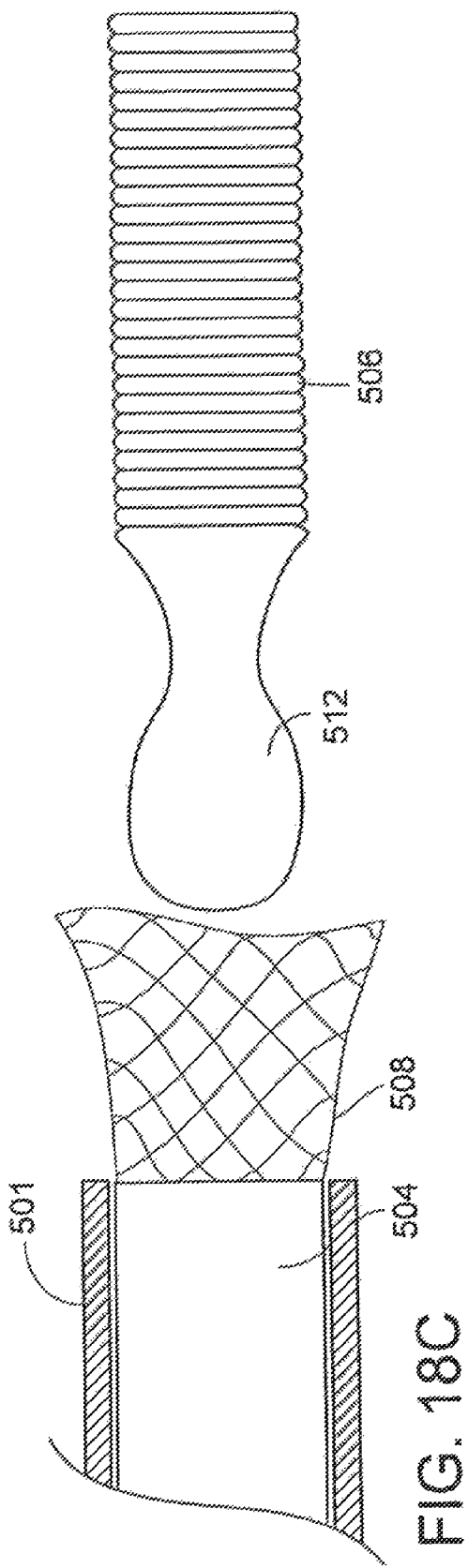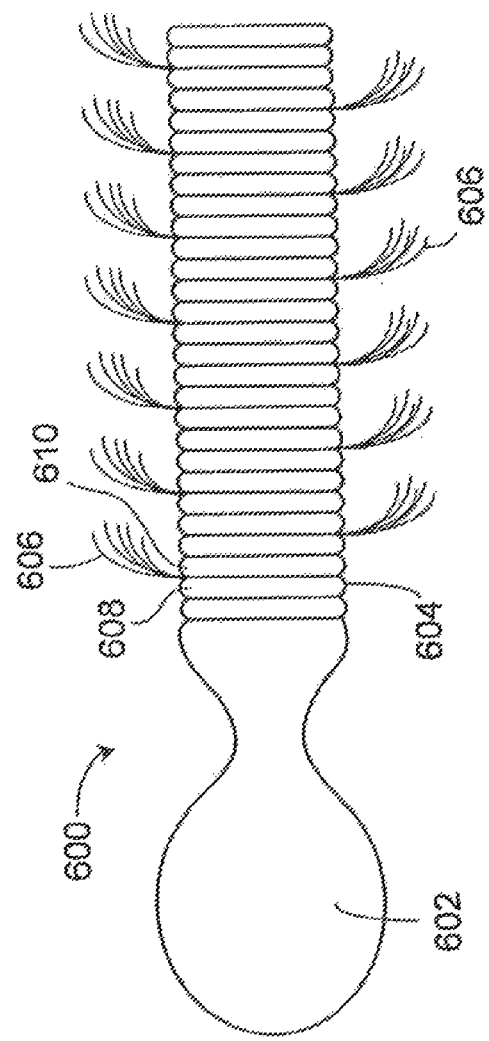

EMBOLIC COILS AND RELATED COMPONENTS, SYSTEMS, AND METHODS

CROSS REFERENCE TO RELATED APPLICATIONS

This application is a continuation of U.S. application Ser. No. 11/425,546, filed on Jun. 21, 2006, now abandoned the entire disclosure of which is incorporated by reference herein for all purposes.

TECHNICAL FIELD

The invention relates to embolic coils, and related components, systems, and methods.

BACKGROUND

Therapeutic vascular occlusions (embolizations) are used to prevent or treat pathological conditions in situ. Embolic coils can be used to occlude vessels in a variety of medical applications. Delivery of embolic coils (e.g., through a catheter) can depend on the size and/or shape or the coils. Some embolic coils include fibers that can, for example, enhance thrombosis at a treatment site.

SUMMARY

In one aspect, the invention features an article that includes an embolic coil and a non-hook-shaped head attached to the embolic coil.

In another aspect, the invention features an embolic coil delivery wire having a non-hook-shaped head.

In an additional aspect, the invention features an article that includes an embolic coil delivery wire and at least two arms extending from the embolic coil delivery wire.

In a further aspect, the invention features an article that includes an embolic coil and at least two arms extending from the embolic coil.

In another aspect, the invention features an article that includes a first coiled wire and a second coiled wire that is co-wound with the first coiled wire. The article is an embolic coil.

In an additional aspect, the invention features an embolic coil system that includes a catheter having a lumen and an article disposed in the lumen of the catheter. The article includes an embolic coil and a non-hook-shaped head attached to the embolic coil.

In a further aspect, the invention features an embolic coil system that includes a catheter having a lumen and an embolic coil delivery wire disposed in the lumen of the catheter. The embolic coil delivery wire has a non-hook-shaped head.

In another aspect, the invention features an embolic coil system that includes a catheter having a lumen, an embolic coil delivery wire disposed in the lumen of the catheter, and at least two arms extending from an end of the embolic coil delivery wire.

In an additional aspect, the invention features an embolic coil system that includes a catheter having a lumen and an article disposed in the lumen of the catheter. The article includes an embolic coil and at least two arms extending from the embolic coil.

In a further aspect, the invention features an article that includes an embolic coil delivery wire and a tubular mesh member attached to the embolic coil delivery wire.

In another aspect, the invention features a method that includes delivering an embolic coil system into a body of a subject. The embolic coil system includes a catheter having a lumen and an article disposed in the lumen of the catheter. The article includes an embolic coil and a non-hook-shaped head attached to the embolic coil.

In an additional aspect, the invention features a method that includes delivering an embolic coil system into a body of a subject. The embolic coil system includes a catheter having a lumen and an embolic coil delivery wire disposed in the lumen of the catheter. The embolic coil delivery wire has a non-hook-shaped head.

In a further aspect, the invention features a method that includes delivering an embolic coil system into a body of a subject. The embolic coil system includes a catheter having a lumen, an embolic coil delivery wire disposed in the lumen of the catheter, and at least two arms extending from an end of the embolic coil delivery wire.

In another aspect, the invention features a method that includes delivering an embolic coil system into a body of a subject. The embolic coil system includes a catheter having a lumen and an article disposed in the lumen of the catheter. The article includes an embolic coil and at least two arms extending from the embolic coil.

In an additional aspect, the invention features a method that includes delivering an embolic coil system into a body of a subject. The embolic coil system includes an embolic coil delivery wire, at least two arms extending from the embolic coil delivery wire, and an embolic coil that is detachably engaged with the arms. The method also includes detaching the embolic coil from the arms of the embolic coil system.

In a further aspect, the invention features a method that includes delivering an embolic coil system into a body of a subject. The embolic coil system includes an embolic coil delivery wire having a non-hook-shaped head, and an embolic coil that is detachably engaged with the non-hook-shaped head. The method also includes detaching the embolic coil from the non-hook-shaped head.

In another aspect, the invention features a method that includes delivering an embolic coil system into a body of a subject. The embolic coil system includes a catheter including a sheath having a lumen, an embolic coil delivery wire disposed in the lumen of the sheath, a tubular mesh member attached to the embolic coil delivery wire, and an embolic coil that is at least partially disposed in a lumen of the tubular mesh member. The method also includes retracting the sheath so that the sheath releases the embolic coil.

Embodiments can also include one or more of the following.

The head can have a longitudinal axis, and can be rotationally symmetric about the longitudinal axis. In some embodiments, the head can be peanut-shaped. The head can have a lumen and/or a groove. The embolic coil delivery wire can include a body, and the head can be attached to the body or can be integrally formed with the body.

The arms can be attached to a distal portion of the embolic coil delivery wire. The arms can be adapted to flex. The arms can form an interference fit within the lumen of the catheter. The arms can be formed of the same material as the embolic coil delivery wire. The article can have an end that includes an arm formed from the first coiled wire and an arm formed from the second coiled wire.

The embolic coil system can include an article including an embolic coil delivery wire that is detachably engaged with the non-hook-shaped head. The article can also include at least two arms extending from the embolic coil delivery wire. At least one of the arms can be detachably engaged with the head of the embolic coil.

The embolic coil system can include an article including an embolic coil, and the article can be detachably engaged with the head of the embolic coil delivery wire. The article can also include at least two arms extending from the embolic coil. At least one of the arms can be detachably engaged with the head of the embolic coil delivery wire.

The embolic coil system can include an embolic coil, and the arms can be detachably engaged with the embolic coil.

The article can include an embolic coil. The tubular mesh member can have a lumen, and the embolic coil can be at least partially disposed in the lumen of the tubular mesh member. In certain embodiments, the embolic coil can have a non-hook-shaped head that is disposed in the lumen of the tubular mesh member.

Embodiments can include one or more of the following advantages.

In some embodiments, an embolic coil or an embolic coil delivery wire can be adapted for use in delivery devices of different sizes. For example, in certain embodiments, an embolic coil delivery wire with multiple arms extending from it can be adapted for use in microcatheters having different inner diameters. In some embodiments, the arms can flex to allow the embolic coil delivery wire or the embolic coil to fit within a lumen of a delivery device (e.g., a catheter).

In certain embodiments, an embolic coil delivery wire with multiple arms extending from it can have enhanced rotational and/or axial flexibility relative to an embolic coil delivery wire that does not have multiple arms extending from it. This enhanced rotational and/or axial flexibility can, for example, allow the embolic coil delivery wire to relatively easily and/or precisely deliver an embolic coil to a target site. In some embodiments, the embolic coil delivery wire can be used to manipulate an embolic coil into a desired position (e.g., by rotating the arms) prior to releasing the embolic coil into a target site.

In certain embodiments, an embolic coil having a non-hook-shaped head can be relatively easy to maneuver and/or to deliver to a target site. As an example, the embolic coil can be detachably engaged with an embolic coil delivery wire (e.g., an embolic coil delivery wire with multiple arms extending from it), which can be used to precisely place the embolic coil at a target site. In some embodiments, after the embolic coil is delivered to a first site, the embolic coil delivery wire can be used to withdraw the embolic coil from the site and to re-position the embolic coil at a second site. The maneuverability of the embolic coil can, for example, allow the embolic coil to be relatively easily packed into a target site.

In certain embodiments, an embolic coil system including a catheter and an embolic coil delivery wire having arms that are engaged with a head of an embolic coil can be used to deliver the embolic coil to a target site relatively easily and/or efficiently. As an example, in some embodiments, the embolic coil system can experience relatively little friction between the embolic coil and the walls of the catheter during delivery of the embolic coil to a target site. As another example, in certain embodiments, the embolic coil system can be used to deliver the embolic coil to a target site without resulting in significant deformation of the shape of the embolic coil. As an additional example, in some embodiments, the embolic coil can assume its secondary shape relatively easily as the embolic coil is being delivered from the catheter.

In some embodiments, an embolic coil having a non-hook-shaped head can be sufficiently radiopaque to be viewed (e.g., by a physician and/or a technician), for example, using X-ray fluoroscopy without using a radiopaque contrast agent. Such an embolic cell may be viewed using a non-invasive technique, and/or may be monitored to determine the progress of a procedure. In certain embodiments, such an embolic coil can be monitored to determine whether the embolic coil is migrating to a site that is not targeted for treatment.

Features and advantages are in the description, drawings, and claims.

DESCRIPTION OF DRAWINGS

FIGS. 2A and 2B illustrate the delivery of an embodiment of an embolic coil to the site of an aneurysm.

FIG. 5A is a side view of an embodiment of an embolic coil.

FIG. 5B is a cross-sectional view of the embolic coil of FIG. 5A, taken along line 5B-5B.

FIGS. 18A-18C illustrate the delivery of an embodiment of an embolic coil from an embodiment of an embolic coil system.

FIG. 19 is a side view of an embodiment of an embolic coil.

DETAILED DESCRIPTION

Figure 1:
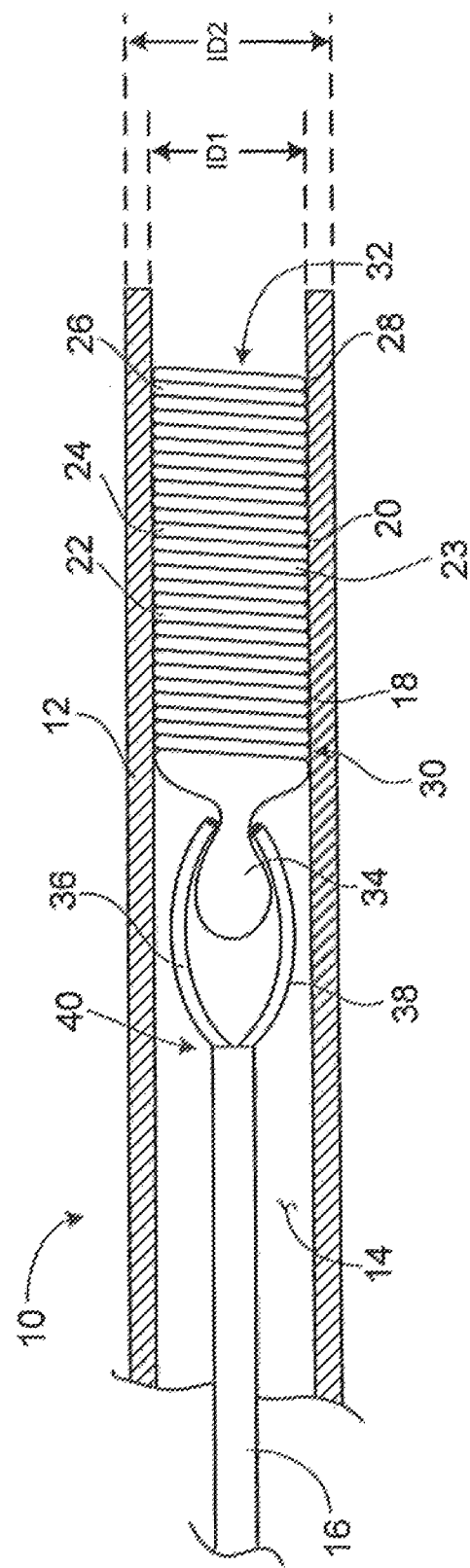
FIG. 1 is a side view in partial cross-section of an embodiment of an embolic coil system.

FIG. 1 shows an embolic coil system 10, which includes a catheter 12 with a lumen 14. An embolic coil delivery wire 16 and an embolic coil 18 that is detachably engaged with embolic coil delivery wire 16 are both disposed within lumen 14. Embolic coil 18 includes an embolic coil body 20 that is formed out of windings (e.g., windings 22, 23, 24, and 26) of a wire 28. Embolic coil body 20 has a proximal end 30 and a distal end 32. Embolic coil 18 also includes a non-hook-shaped head (as shown, a peanut-shaped head 34) that is attached to proximal end 30 of embolic coil body 20. Two arms 36 and 38 extend from the distal end 40 of embolic coil delivery wire 16. Arms 36 and 38, which are detachably engaged with head 34 of embolic coil 18, form an interference fit within lumen 14 of catheter 12. In some embodiments, when embolic coil delivery wire 16 and embolic coil 18 are disposed within lumen 14 of catheter 12, a fluid (e.g., a saline solution, a contrast agent, a heparin solution) can also be disposed within lumen 14.

Arms 36 and 38 are capable of flexing, such that they can fit within the lumens of catheters having a range of different inner diameters. As shown in FIG. 1, catheter 12 has an inner diameter ID1 and an outer diameter OD1. In some embodiments, inner diameter ID1 can be at least 0.018 inch (e.g., at least 0.021 inch, at least 0.027 inch, at least 0.03 inch) and/or at most 0.035 inch (e.g., at most 0.03 inch, at most 0.027 inch, at most 0.021 inch). As an example, in certain embodiments, inner diameter ID1 can be 0.021 inch. An example of a catheter having an inner diameter of 0.021 inch is the Renegade® 18 Microcatheter (from Boston Scientific Corp.). As another example, in some embodiments, inner diameter ID1 can be 0.027 inch. An example of a catheter having an inner diameter of 0.027 inch is the Renegade® Hi-Flo™ Microcatheter (from Boston Scientific Corp.). In certain embodiments, outer diameter OD1 can be at least about 0.024 inch and/or at most about 0.05 inch.

FIGS. 2A and 2B show the use of embolic coil 18 to fill and occlude an aneurysmal sac 52 formed in a wall 54 of a lumen 50 of a subject. As shown in FIG. 2A, embolic coil system 10 is delivered into lumen 50 of the subject. As shown in FIG. 2B, embolic coil delivery wire 16 and arms 36 and 38 are used to push embolic coil 18 out of catheter 12. When arms 36 and 38 are released from catheter 12, they open up, thereby releasing embolic coil 18 into aneurysmal sac 52. Embolic coil 18 partially fills aneurysmal sac 52 after embolic coil 18 has been pushed out of catheter 12 by embolic coil delivery wire 16 and arms 36 and 38. By partially filling aneurysmal sac 52, embolic coil 18 helps to occlude aneurysmal sac 52. In some embodiments, after embolic coil 18 has been delivered into aneurysmal sac 52, one or more additional embolic coils can be delivered into aneurysmal sac 52.

Embolic coils can generally be used in a number of different applications, such as neurological applications and/or peripheral applications. In some embodiments, embolic coils can be used to embolize a lumen of a subject (e.g., to occlude a vessel), and/or to treat an aneurysm (e.g., an intercranial aneurysm), an arteriovenous malformation (AVM), a traumatic fistula, uterine fibroids, and/or cancer (e.g., cervical cancer). In certain embodiments, embolic coils can be used in an AAA (abdominal aortic aneurysm) application. In some embodiments, embolic coils can be used to embolize a tumor (e.g., a liver tumor), and/or can be used in transarterial chemoembolization (TACE). In certain embodiments, embolic coils can be used to occlude a lumbar artery and/or to embolize a spleen (e.g., after a portion of the spleen has ruptured). In some embodiments, embolic coils can be used in a portal vein embolization (PVE) procedure.

Figure 3A:
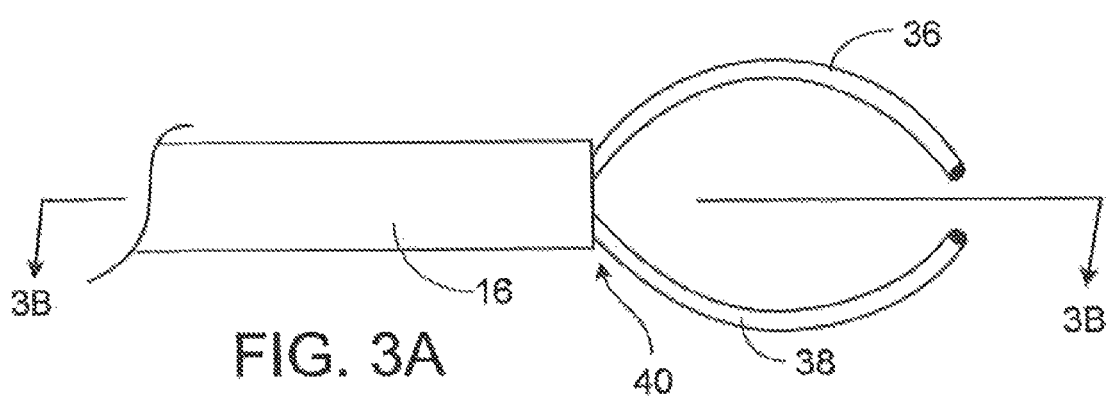
FIG. 3A is a side view of an embodiment of an embolic coil delivery wire.
Figure 3B:
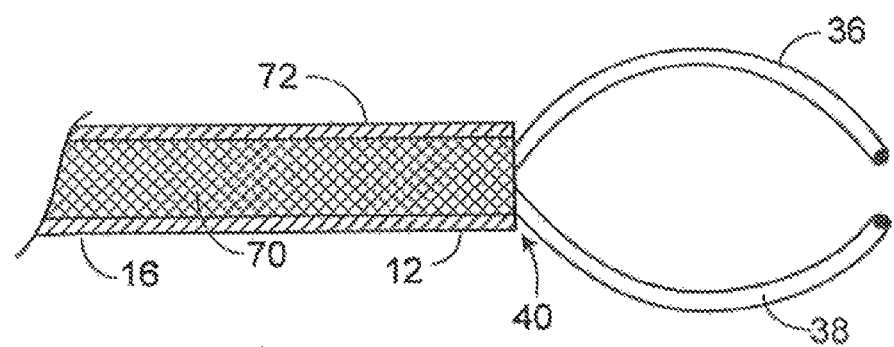
FIG. 3B is a cross-sectional view of the embolic coil delivery wire of FIG. 3A, taken along line 3B-3B.

FIGS. 3A and 3B provide enlarged views of embolic coil delivery wire 16 and arms 36 and 38. As shown in FIG. 3B, embolic coil delivery wire 16 includes a wire portion 70 and a sheath 72 surrounding wire portion 70. Wire portion 70 is attached to arms 36 and 38 at the distal end 40 of embolic coil delivery wire 16. In certain embodiments, wire portion 70 can be soldered (e.g., gold soldered) to arm 36 and/or arm 38. In some embodiments, wire portion 70 can be resistance welded to arm 36 and/or arm 38.

Wire portion 70 and arms 36 and/or 38 can be formed of the same material or different materials, such as metals (e.g., platinum) and/or metal alloys (e.g., stainless steel). In some embodiments, wire portion 70 and arms 36 and/or 38 can be formed of an iridium-platinum alloy (e.g., 10 percent iridium/90 percent platinum).

In certain embodiments, sheath 72 can be formed of tetrafluoroethylene (TFE). This can, for example, cause sheath 72 to be relatively lubricious. In some embodiments, as the lubricity of sheath 72 increases, the maneuverability of embolic coil delivery wire 16 within lumen 14 of catheter 12 can also increase. Embolic coil delivery wire 16 can be relatively flexible, which can reduce the likelihood of perforation of a delivery device wall and/or a body lumen wall.

Figure 4:
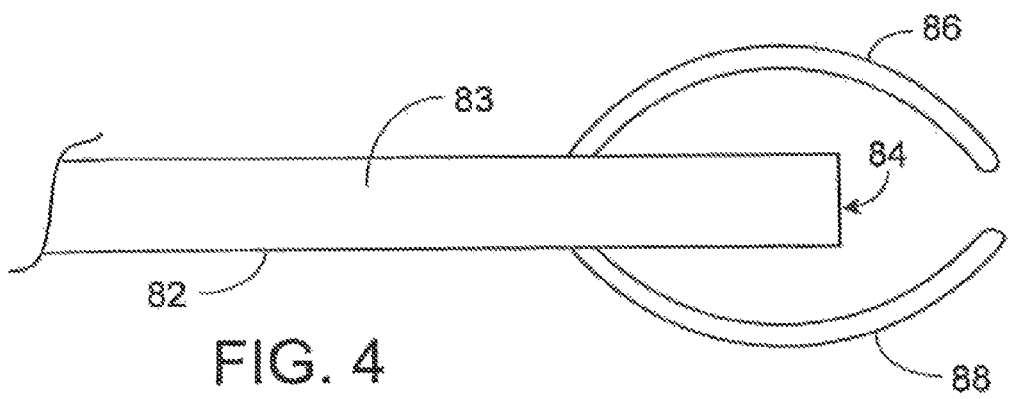
FIG. 4 is a side view of an embodiment of an embolic coil delivery wire.

While embolic coil delivery wire 16 includes a wire portion 70 surrounded by a sheath 72, in some embodiments, an embolic coil delivery wire may not include a sheath. Additionally, while embolic coil delivery wire 16 includes arms 36 and 38 that are attached to wire portion 70 at distal end 40 of embolic coil delivery wire 16, in certain embodiments, one or more arms can be attached to an embolic coil delivery wire in a different location. As an example, FIG. 4 shows an embolic coil delivery wire 82 including a wire portion 83 having a distal end 84, and two arms 86 and 88 extending from wire portion 83 at a location that is proximal to distal end 84. Arms 86 and 88 are directly bonded to wire portion 83. Embolic coil delivery wire 82 does not include a sheath.

FIGS. 5A and 5B show enlarged views of embolic coil 18. As shown in FIGS. 5A and 5B, peanut-shaped head 34 is rotationally symmetric about a longitudinal axis LA1 of head 34. As shown in FIG. 5B, head 34 includes an attachment region 90 to which embolic coil body 20 is attached (e.g., welded). Head 34 and embolic coil body 20 can be formed of the same material or of different materials, such as metals, metal alloys, and/or polymers. In certain embodiments in which head 34 and embolic coil body 20 are formed of the same metals and/or metal alloys, head 34 and embolic coil body 20 can be relatively corrosion-resistant.

Examples of metals include platinum, tungsten, tantalum, palladium, lead, gold, titanium, and silver. Examples of metal alloys include stainless steel, alloys of tungsten, alloys of tantalum, alloys of platinum (e.g., platinum-tungsten alloys such as 92 percent platinum/eight percent tungsten, platinum-iridium alloys such as 92 percent platinum/eight percent iridium), alloys of palladium, alloys of lead, alloys of gold, alloys of titanium, alloys of silver, and cobalt-chromium alloys (e.g., Elgiloy® alloy, from Elgiloy Specialty Materials). Examples of polymers include polyolefins, polyurethanes, block copolymers, polyethers, and polyimides. Other examples of polymers are disclosed, for example, in Buiser et al., U.S. patent application Ser. No. 11/311,617, filed on Dec. 19, 2005, and entitled "Coils", which is incorporated herein by reference.

In some embodiments, it may be desirable to observe embolic coil 18 using X-ray fluoroscopy. In some such embodiments, head 34 and/or embolic coil body 20 can include one or more radiopaque materials that can enhance the visibility of head 34 and/or embolic coil body 20 under X-ray fluoroscopy. As an example, embolic coil body 20 may be formed of a radiopaque material. As another example, peanut-shaped head 34 may be formed of a material (e.g., a metal, a polymer) that encapsulates a radiopaque material, and/or may be formed of a material (e.g., a metal, a polymer) within which a radiopaque material is disposed. As an additional example, peanut-shaped head 34 may include a coating of a radiopaque material.

As used herein, a radiopaque material refers to a material having a density of about ten grams per cubic centimeter or greater (e.g., about 25 grams per cubic centimeter or greater, about 50 grams per cubic centimeter or greater). A radiopaque material can be, for example, a metal, a metal alloy, a metal oxide (e.g., titanium dioxide, zirconium oxide, aluminum oxide), bismuth subcarbonate, or barium sulfate. In some embodiments, a radiopaque material is a radiopaque contrast agent. Examples of radiopaque contrast agents include Omnipaque™, Renocal®, iodiamide meglumine, diatrizoate meglumine, ipodate calcium, ipodate sodium, iodamide sodium, iothalamate sodium, iopamidol, and metrizamide. Radiopaque contrast agents are commercially available from, for example, Bracco Diagnostic. Radiopaque materials are described, for example, in Rioux et al., U.S. Patent Application Publication. No. US 2004/0101564 A1, published on May 27, 2004, and entitled "Embolization", which is incorporated herein by reference.

In some embodiments, head 34 and/or embolic coil body 20 can be formed out of one or more shape-memory materials, such as shape-memory metal alloys and/or shape-memory polymers. An example of a shape-memory metal alloy is Nitinol. Examples of shape-memory polymers include shape-memory polyurethanes and the Veriflex™ two-part thermoset shape-memory polymer resin system (from CRG Industries, Dayton, Ohio).

In certain embodiments, head 34 and/or embolic coil body 20 can be formed of one or more bioerodible materials. Examples of bioerodible materials include polylactic acid (PLA), polyglycolic acid (PGA), polysaccharides (e.g., alginate), water soluble polymers (e.g., polyvinyl alcohol, such as polyvinyl alcohol that has not been cross-linked), biodegradable poly DL-lactide-poly ethylene glycol (PELA), hydrogels (e.g., polyacrylic acid, hyaluronic acid, gelatin such as gelatin foam, carboxymethyl cellulose), polyethylene glycol (PEG), chitosan, polyesters (e.g., polycaprolactones), poly(lactic-co-glycolic) acid (e.g., a poly(d-lactic-co-glycolic) acid), polyamino acids, polynucleic acids, polyhydroxyalkanoates, polyanhydrides, and combinations thereof.

As shown in FIGS. 5A and 5B, embolic coil 18 in its primary shape has a length L1. In some embodiments, length L1 can be at least about two millimeters (e.g., at least about 10 millimeters, at least about 50 millimeters, at least about 100 millimeters, at least about 250 millimeters) and/or at most about 500 millimeters (e.g., at most about 250 millimeters, at most about 100 millimeters, at most about 50 millimeters, at most about 10 millimeters).

As shown in FIG. 5B, embolic coil body 20 has an inner diameter ID2 and an outer diameter OD2. In some embodiments, inner diameter ID2 can be at least 0.006 inch (e.g., at least 0.01 inch, at least 0.02 inch) and/or at most 0.028 inch (e.g., at most 0.02 inch, at most 0.01 inch). In certain embodiments, outer diameter OD1 can be at least 0.01 inch (e.g., at least 0.02 inch, at least 0.03 inch) and/or at most 0.038 inch (e.g., at most 0.03 inch, at most 0.02 inch).

The pitch of an embolic coil body is the sum of the thickness of one winding of wire (e.g., winding 22 of wire 28) and the amount of space between that winding and a consecutive winding of wire (e.g., winding 23 of wire 28). FIG. 5A shows the pitch P1 of embolic coil body 20. Because the windings of embolic coil body 20 are flush with each other, pitch P1 of embolic coil body 20 is equal to the thickness of one winding of embolic coil body 20. In some embodiments, pitch P1 can be at most 0.004 inch and/or at least 0.002 inch.

In general, embolic coil 18 has a primary shape and a secondary shape. Embolic coil 18 exhibits only its primary shape when embolic coil 18 is extended within lumen 14 of catheter 12 (as shown in FIG. 1). As embolic coil 18 exits catheter 12, however, embolic coil 18 further assumes its secondary shape, which can, for example, allow embolic coil 18 to fill a target site (e.g., an aneurysmal sac). Typically, the primary shape of embolic coil 18 can be selected for deliverability, and the secondary shape of embolic coil 18 can be selected for application (e.g., embolization of an aneurysm).

As FIGS. 6-12 illustrate, an embolic coil can have any of a number of different secondary shapes, which can depend on the particular application for the embolic coil.

Figure 6:
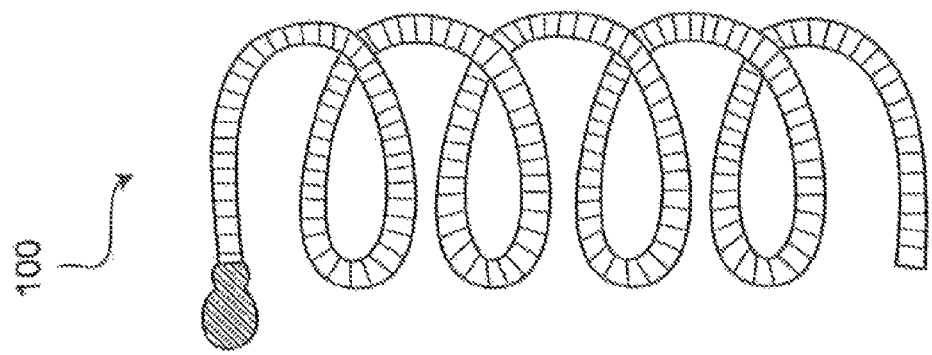
FIG. 6 is a perspective view of an embodiment of an embolic coil.

For example, FIG. 6 shows an embolic coil 100 with a spiral secondary shape, which can be used, for example, to provide a supportive framework along a vessel wall. Alternatively or additionally, an embolic coil with a spiral secondary shape can be used to hold ether embolic coils that are subsequently delivered to the target site.

Figure 7:
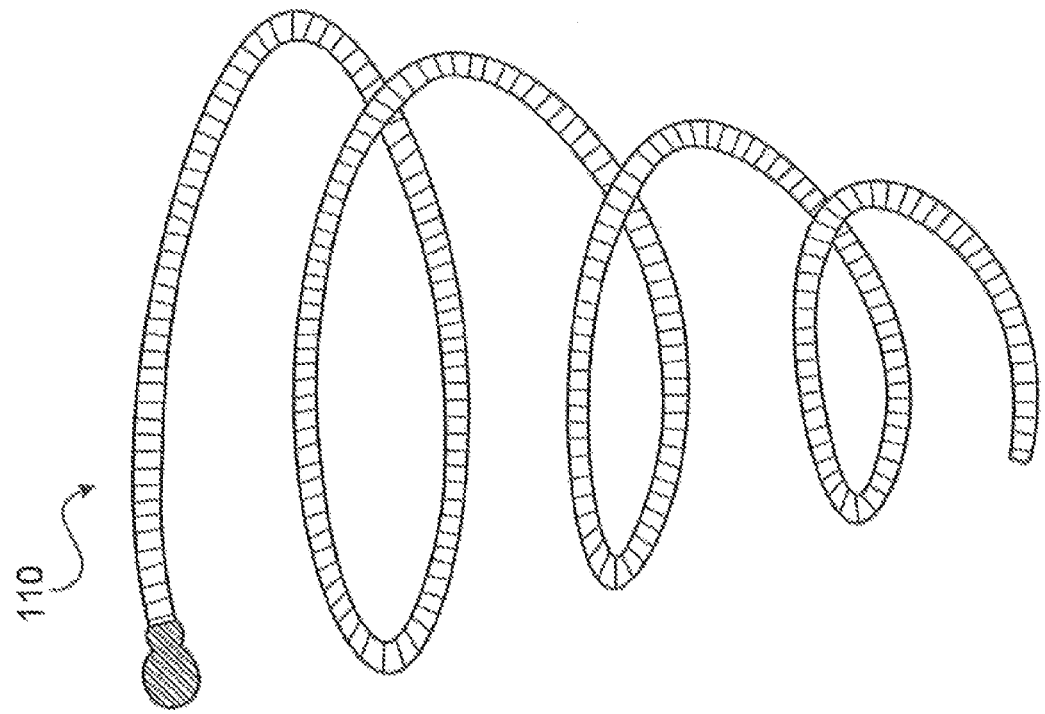
FIG. 7 is a perspective view of an embodiment of an embolic coil.

FIG. 7 shows an embolic coil 110 with a single apex vortex secondary shape, which can be used, for example, to close the center of a target site (e.g., a vessel, an aneurysm) that is to be occluded, and/or to occlude a target site in conjunction with an embolic coil such as embolic coil 100 (FIG. 6). An embolic coil with a single apex vortex secondary shape can be used to occlude a vessel having low flow, intermediate flow, or high flow. In some embodiments, multiple embolic coils with single apex vortex secondary shapes can be used to occlude a vessel. In certain embodiments, an embolic coil with a single apex vortex secondary shape can be used as a packing coil, such that the coil can be packed into a vessel that is slightly smaller than the diameter of the coil. As an example, a six-millimeter diameter coil can be packed into a vessel having a five-millimeter diameter. In some embodiments, an embolic coil with a single apex vortex secondary shape can be used to embolize tumor and/or to treat gastrointestinal bleeding.

Figure 8:
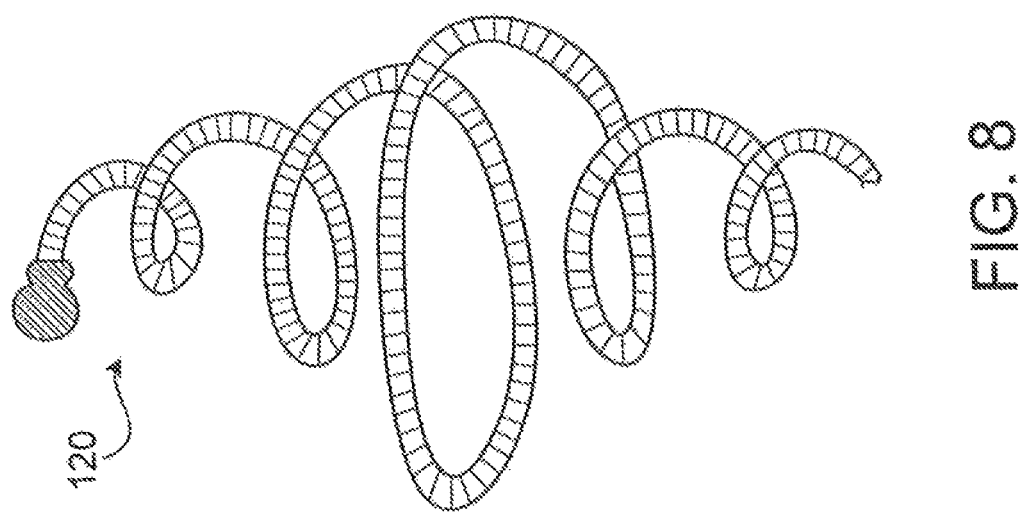
FIG. 8 is a perspective view of an embodiment of an embolic coil.

As shown in FIG. 8, an embolic coil 120 can have a dual apex vortex secondary shape (also known as a diamond secondary shape), which, like the single apex vortex secondary shape, can used, for example, to close the center of a target site (e.g., a vessel, an aneurysm) that is to be occluded, and/or to occlude a target site in conjunction with an embolic coil such as embolic coil 100 (FIG. 6). An embolic coil with a dual apex vortex secondary shape can be used to occlude a vessel having low flow, intermediate flow, or high flow, and can be used alone or in combination with other embolic coils (e.g., other embolic coils having dual apex vortex secondary shapes). In certain embodiments, an embolic coil with a dual apex vortex secondary shape can be used as a packing coil. In some embodiments, an embolic coil with a dual apex vortex secondary shape can be used to embolize a tumor and/or to treat gastrointestinal bleeding.

Figure 9:
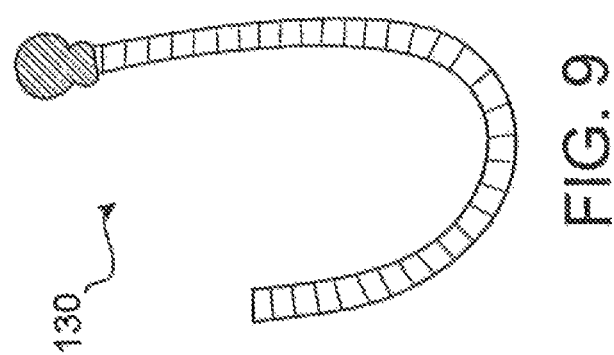
FIG. 9 is a perspective view of an embodiment of an embolic coil.

FIG. 9 shows an embolic coil 130 with a secondary shape in the form of a J, which can be used, for example, to fill remaining space in an aneurysm that was not filled by other coils. In some embodiments, an operator (e.g., a physician) can hook the curved portion of embolic coil 130 into a coil or coil mass that has already been deployed at a target site, and then shape the straighter portion of coil 130 to fill the target site.

Figure 10A:
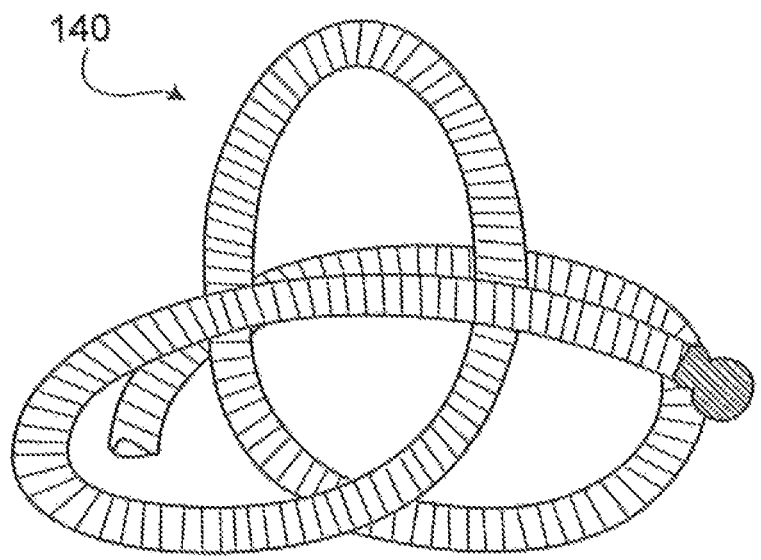
FIG. 10A is a front view of an embodiment of an embolic coil.
Figure 10B:
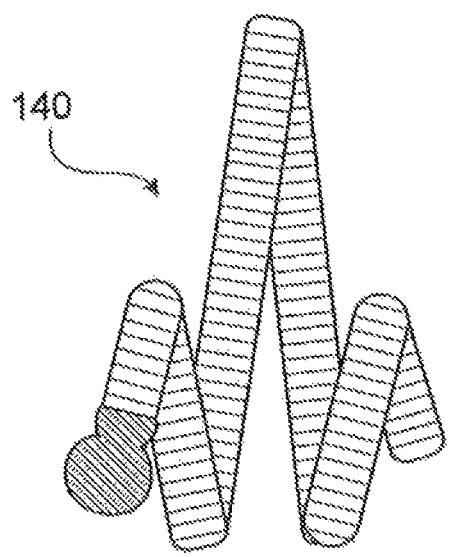
FIG. 10B is a side view of an embolic coil of FIG. 10A.

FIGS. 10A and 10B show an embolic coil 140 having a complex helical secondary shape. An embolic cell with a complex helical secondary shape can be used, for example, to frame a target site. In certain embodiments, an embolic coil with a complex helical secondary shape can be used as an anchoring coil that helps to hold other embolic coils in place at a target site (e.g., thereby allowing additional embolic coils to be packed into the target site).

Figure 11A:
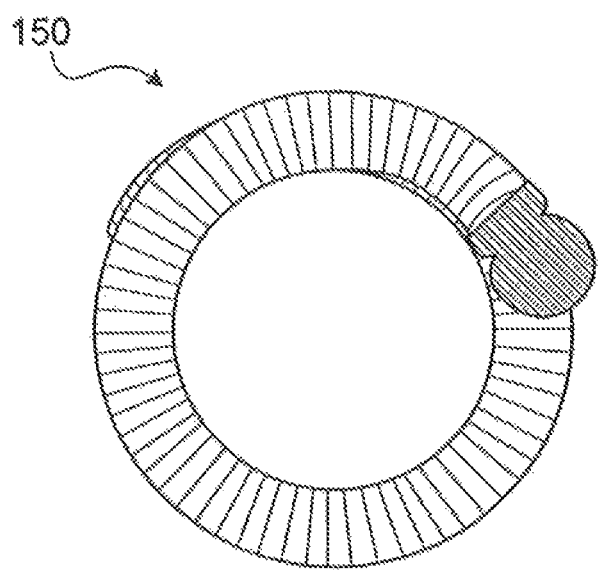
FIG. 11A is a front view of an embodiment of an embolic coil.
Figure 11B:
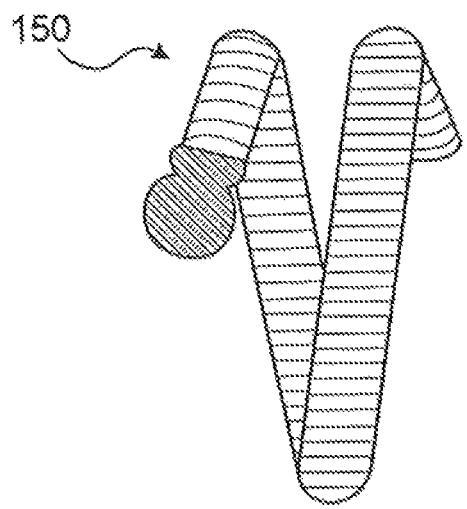
FIG. 11B is a side view of the embolic coil of FIG. 11A.

FIGS. 11A and 11B show an embolic coil 150 having a helical secondary shape. An embolic coil with a helical secondary shape can be used, for example, as a packing coil.

Figure 12:
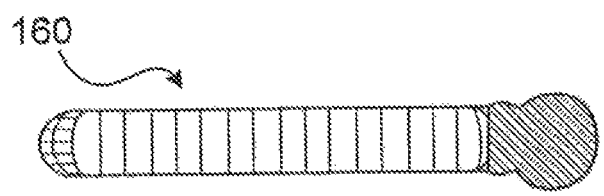
FIG. 12 is a side view of an embodiment of an embolic coil.

FIG. 12 shows an embolic coil 160 having a straight secondary shape. An embolic coil with a straight secondary shape can be used, for example, in a relatively small vessel (e.g., to block blood flow to a tumor).

Figure 13:
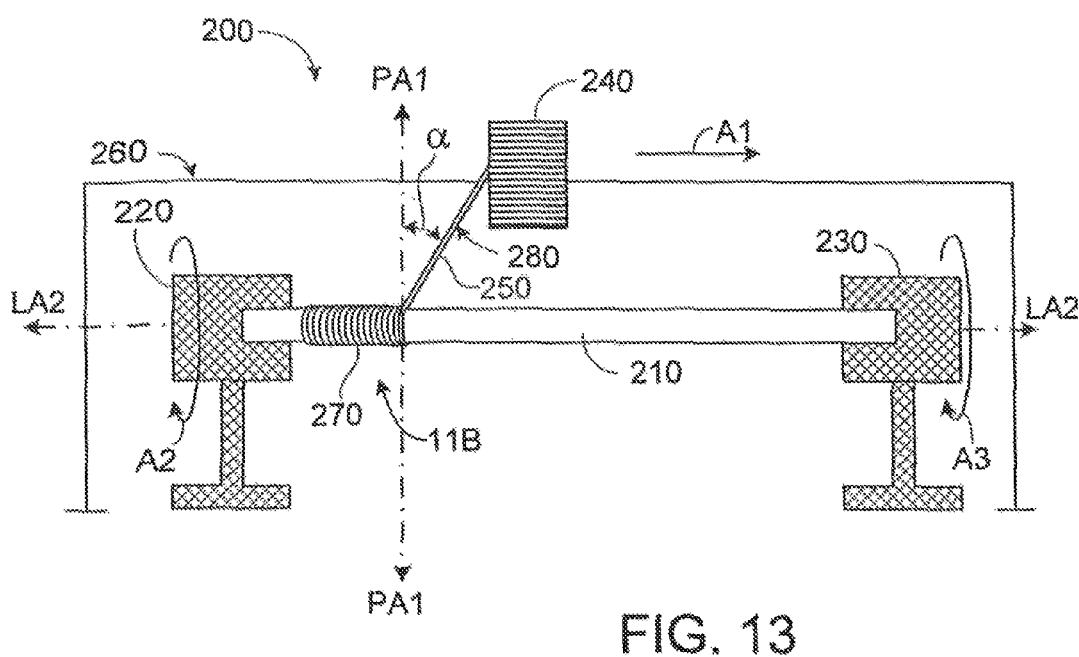
FIG. 13 is a side view of an embodiment of a process for forming an embolic coil.
Figure 14A:
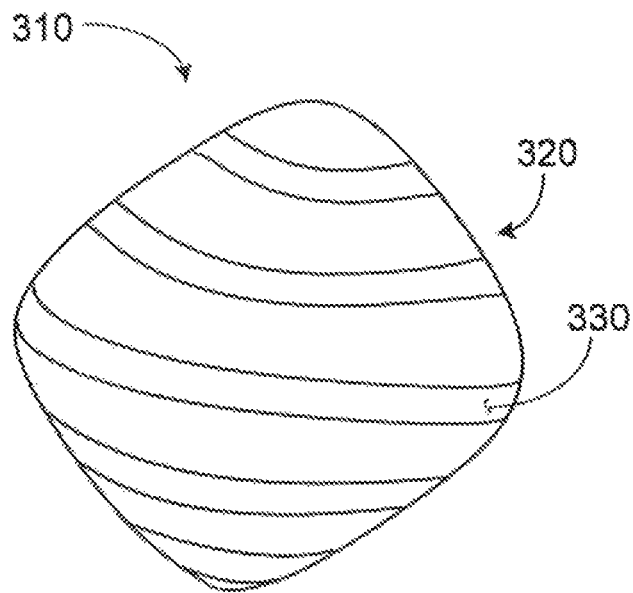
FIG. 14A is a side view of an embodiment of a mandrel.
Figure 14B:
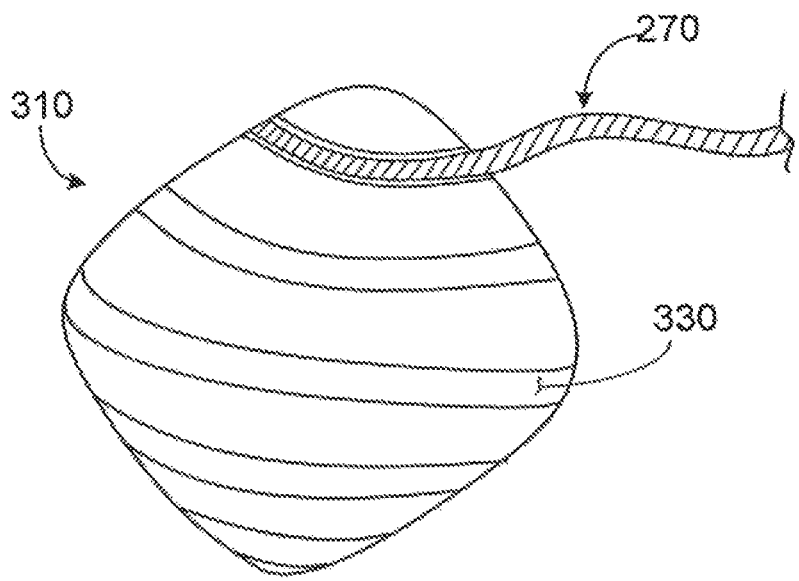
FIGS. 14B and 14C are illustrations of an embodiment of a process for forming an embolic coil using the mandrel of FIG. 14A.
Figure 14C:
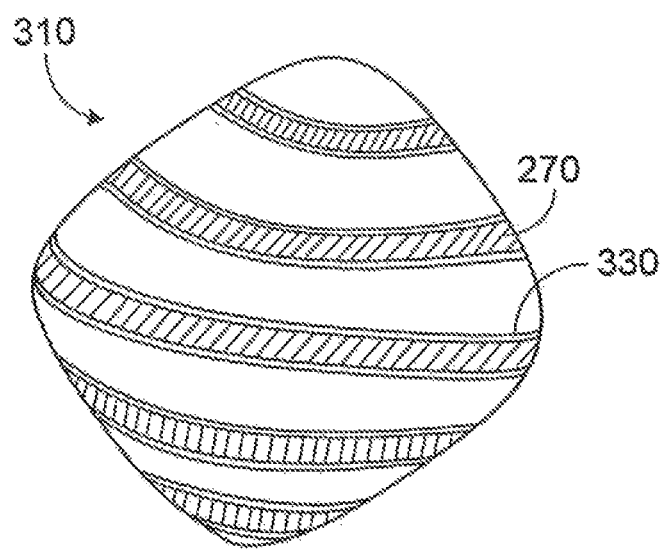

FIG. 13 illustrates a process for forming an embolic coil (e.g., embolic coil 18) in its primary shape, and FIGS. 14A-14C show a process for forming the secondary shape of the embolic coil.

As shown in FIG. 13, a coil-forming apparatus 200 includes a mandrel 210 held by two rotatable chucks 220 and 230. A spool 240 of wire 28 is disposed above mandrel 210, and is attached to a linear drive 260. To form an embolic coil in its primary shape, chucks 220 and 230 are activated so that they rotate in the direction of arrows A2 and A3, thereby rotating mandrel 210. Linear drive 260 also is activated, and moves spool 240 in the direction of arrow A1. The rotation of mandrel 210 pulls wire 28 from spool 240 at a predetermined pull-off angle, and causes wire 28 to wrap around mandrel 210, forming a coil 270.

As FIG. 13 shows, the pull-off angle ($\alpha$) is the angle between axis PA1, which is perpendicular to longitudinal axis LA2 of mandrel 210, and the portion 280 of wire 28 between spool 240 and coil 270. In some embodiments, $\alpha$ can be from about one degree to about six degrees (e.g., from about 1.5 degrees to about five degrees, from about 1.5 degrees to about 2.5 degrees, about two degrees). In certain embodiments, a controller (e.g., a programmable logic controller) can be used to maintain the pull-off angle in coil-forming apparatus 200. Because mandrel 210 is rotating as it is pulling wire 28 from spool 240, and because linear drive 260 is moving spool 240 in the direction of arrow A1, wire 28 forms coil 270 in a primary shape around mandrel 210. Coil 270 can be formed, for example, at room temperature (25° C.).

After coil 270 has been formed, chucks 220 and 230, and linear drive 260, are deactivated, and portion 280 of wire 28 is cut. Mandrel 210 is then released from chuck 220, and coil 270 is pulled off of mandrel 210. While coil 270 might lose some of its primary shape as it is pulled off of mandrel 210, coil 270 can generally return to its primary shape shortly thereafter, because of memory imparted to coil 270 during formation. In some embodiments, after coil 270 has been removed from mandrel 210, one or both of the ends of coil 270 can be heated and melted to form rounder, more biocompatible (e.g., atraumatic) ends.

Mandrel 210 can be formed of, for example, a metal or a metal alloy, such as stainless steel. In some embodiments, mandrel 210 can be formed of one or more polymers, such as Teflon® (polytetrafluoroethylene) or Delrin® (polyoxymethylene). In certain embodiments, mandrel 210 can be formed of a shape-memory material, such as Nitinol.

The tension of mandrel 210 as it is held between chucks 220 and 230 preferably is sufficiently high to avoid vibration of mandrel 210 during the winding process, and sufficiently low to avoid stretching of mandrel 210 during the winding process. In some instances, significant stretching of mandrel 210 during the winding process could cause coil 270 to have a smaller primary shape than desired, and/or could make it relatively difficult to remove coil 270 from mandrel 210. In certain embodiments, the tension of mandrel 210 can be from about 100 grams to about 1,000 grams (e.g., from about 300 grams to about 600 grams, from about 400 grams to about 500 grams). For example, the tension of mandrel 210 can be about 506 grams.

In some embodiments, wire 28 can be wound around mandrel 210 at a tension of at least about four grams (e.g., at least about five grams, at least about six grams, at least about 10 grams, at least about 22 grams, at least about 27 grams, at least about 32 grams, at least about 40 grams, at least about 60 grams, at least about 65 grams, at least about 85 grams) and/or at most about 100 grams (e.g., at most about 85 grams, at most about 65 grams, at most about 60 grams, at most about 40 grams, at most about 32 grams, at most about 27 grams, at most about 22 grams, at most about 10 grams, at most about six grams, at most about five grams).

In certain embodiments, the length of coil 270 in its primary shape and while under tension on mandrel 210 can be from about 10 centimeters to about 250 centimeters (e.g., from about 50 centimeters to about 200 centimeters, from about 130 centimeters to about 170 centimeters, from about 144 centimeters to about 153 centimeters, from about 147 centimeters to about 153 centimeters). For example, the length of coil 270 in its primary shape and while under tension on mandrel 210 can be about 132 centimeters or about 147 centimeters. Coil 270 may recoil to some extent (e.g., by at most about five centimeters) when portion 280 of wire 28 is severed, such that coil 270 will be somewhat smaller once it has been removed from mandrel 210. In some embodiments, coil 270 can have a length of from about five centimeters to about 225 centimeters (e.g., from about 25 centimeters to about 170 centimeters, from about 120 centimeters to about 140 centimeters, from about 137 centimeters to about 140 centimeters) after being removed from mandrel 210. After coil 270 has been removed from mandrel 210, coil 270 can be cut into smaller coils.

Once coil 270 has been formed in its primary shape, coil 270 can be further shaped into a secondary shape, as shown in FIGS. 14A-14C.

FIG. 14A shows a mandrel 310 used to form the secondary shape of coil 270. While mandrel 310 is shaped to form a diamond, other types of mandrels can be used to form other secondary shapes. Mandrel 310 is formed of a diamond-shaped block 320 with grooves 330 cut into its surface. As shown in FIGS. 14B and 14C, coil 270 in its primary shape is wrapped around mandrel 310, such that coil 270 fills grooves 330, creating the secondary shape. The ends of coil 270 are then attached (e.g., pinned) to mandrel 310, and coil 270 is heat-treated to impart memory to coil 270. In some embodiments, coil 270 can be heat-treated at a temperature of at least about 1000° F. (e.g., at least about 1050° F., at least about 1100° F., at least about 1150° F.), and/or at most about 1200° F. (e.g., at most about 1150° F., at most about 1100° F., at most about 1050° F.). In certain embodiments, the heat treatment of coil 270 can last for a period of from about 10 minutes to about 40 minutes (e.g., about 25 minutes). After being heat-treated, coil 270 is enwrapped from mandrel 310. The removal of coil 270 from mandrel 310 allows coil 270 to reassume its secondary shape. In some embodiments, after coil 270 has been removed from mandrel 310, one or both of the ends of coil 270 can be heated and melted to form rounder, more biocompatible (e.g., atraumatic) ends.

Mandrel 310 can be formed of, for example, a metal or a metal alloy (e.g., stainless steel). In some embodiments, mandrel 310 can be formed of a plated metal or a plated metal alloy (e.g., chrome-plated stainless steel).

Before, during, or after the formation of the secondary shape of coil 270, a head can be attached (e.g., welded) to coil 270. The head can be formed, for example, using a micromachining process and/or an etching process.

Embolic coils and methods of making embolic coils are described, for example, in Elliott et al., U.S. Patent Application Publication No. US 2006/0116711 A1, published on Jun. 1, 2006, and entitled "Embolic Coils", which is incorporated herein by reference.

In some embodiments, an embolic coil such as embolic coil 18 can include one or more therapeutic agents (e.g., drugs). For example, wire 28 can include one or more therapeutic agents (e.g., dispersed within and/or encapsulated by the material of wire 28), can be coated with one or more therapeutic agents, and/or can be coated with one or more coatings including one or more therapeutic agents. In some embodiments, the therapeutic agents can be dispersed within, and/or encapsulated by, the coatings. Embolic coil 18 can, for example, be used to deliver the therapeutic agents to a target site.

In certain embodiments in which embolic coil 18 is coated by one or more coatings including one or more therapeutic agents, the coatings can include one or more bioerodible and/or bioabsorbable materials. When the coatings are eroded and/or absorbed, they can release the therapeutic agents into the body of a subject (e.g., during delivery and/or at a target site).

In some embodiments, a therapeutic agent-coated embolic coil can include a coating (e.g., a bioerodible and/or bioabsorbable polymer coating) over the surface of the therapeutic agent. The coating can assist in controlling the rate at which therapeutic agent is released from the embolic coil. For example, the coating can be in the form of a porous membrane. The coating can delay an initial burst of therapeutic agent release. The coating can be applied by dipping or spraying the embolic coil. The coating can include therapeutic agent or can be substantially free of therapeutic agent. The therapeutic agent in the coating can be the same as or different from a therapeutic agent on a surface layer of the embolic coil and/or within the embolic coil (e.g., within a wire forming the embolic coil). A polymer coating (e.g., that is bioerodible and/or bioabsorbable) can be applied to an embolic coil surface and/or to a coated embolic coil surface in embodiments in which a high concentration of therapeutic agent has not been applied to the embolic coil surface or to the coated embolic coil surface.

Coatings are described, for example, in Buiser et al., U.S. patent application Ser. No. 11/311,617, filed on Dec. 19, 2005, and entitled "Coils", and in DiMatteo et al., U.S. Patent Application Publication No. US 2004/0076582 A1, published on Apr. 22, 2004, and entitled "Agent Delivery Particle", both of which are incorporated herein by reference.

In some embodiments, one or more embolic coils can be disposed in one or more liquid therapeutic agents.

Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; gene therapies; nucleic acids with and without carrier vectors (e.g., recombinant nucleic acids, DMA (e.g., naked DMA), cDNA, RNA, genomic DNA, cDNA or RNA in a non-infectious vector or in a viral vector which may have attached peptide targeting sequences, antisense nucleic acids (RNA, DNA)); peptides (e.g., growth factor peptides, such as basic fibroblast growth factor (bFGF)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase); immunologic species; nonsteroidal anti-inflammatory medications; chemoagents; pain management therapeutics; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death (e.g., anti-apoptotic Bcl-2 family factors and Akt kinase).

Exemplary non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists anti-thrombin antibodies, anti-platelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in Kunz et al., U.S. Pat. No. 5,733,925, assigned to NeoRx Corporation, which is incorporated herein by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

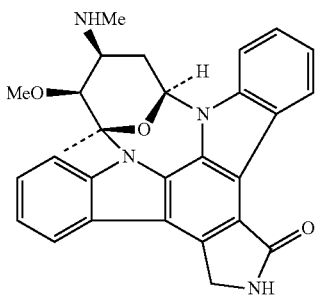 [SMILES: CN[C@H]1C[C@H]2O[C@@](C)([C@H]1OC)n1c3ccccc3c3c4c(c5c6ccccc6n2c5c31)C(=O)NC4]

as well as diindoloalkaloids having one of the following general structures:

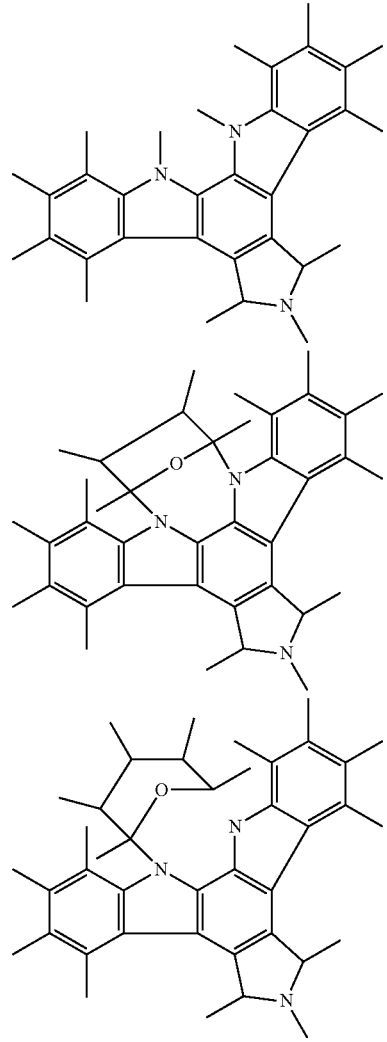

as well as simulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DMA topoisomerase II and DNA polymerase, RNA polymerase, adenyl guanyl cyclase), superoxide dismutase inhibitors, terminal deoxynucleotidyl-transferase, reverse transcriptase, anti-sense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes; e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin B (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including α-antagonists (e.g., prazosin, bunazosine), β-antagonists (e.g., propranolol), and α/β-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP IIb/IIIa inhibitors (e.g., abciximab, epitifibatide, tirofiban, intergrilin); coagulation pathway modulators, including heparinoids (e.g., heparin, low molecular weight heparin, dextran sulfate, β-cyclodextrin tetradecasulfate), thrombin inhibitors (e.g., hirudin, hirulog, PPACK (D-phe-L-propyl-L-arg-chloromethylketone), argatroban), FXa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-β pathway agents such as polyanionic agents (heparin, fucoidin), decorin, and TGF-β antibodies, EGF pathway agents (e.g., EGF antibodies, receptor antagonists, chimeric fusion proteins), TNF-α pathway agents (e.g., thalidomide and analogs thereof), thromboxane, A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganic ions (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, anti-sense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

Therapeutic agents are described, for example, in Buiser et al., U.S. patent application Ser. No. 11/311,617, filed on Dec. 19, 2005, and entitled "Coils"; DiMatteo et al., U.S. Patent Application Publication No. US 2004/0076582 A1, published on Apr. 22, 2004, and entitled "Agent Delivery Particle"; Pinchuk et al., U.S. Pat. No. 6,545,097; and Schwarz et al., U.S. Pat. No. 6,368,658, all of which are incorporated herein by reference.

While certain embodiments have been described, other embodiments are possible.

Figure 15A:
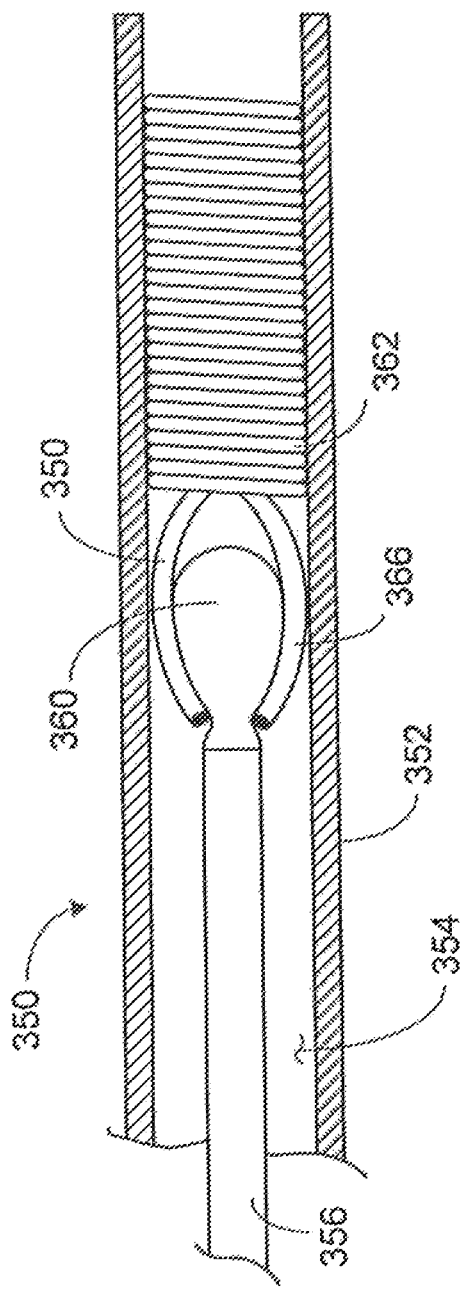
FIG. 15A is a side view in partial cross-section of an embodiment of an embolic coil system.

As an example, in some embodiments, an embolic coil can have at least two arms extending from it, and in certain embodiments, an embolic coil delivery wire can have a non-hook-shaped head (e.g., a peanut-shaped head). For example, FIG. 15A shows an embolic coil system 350 including a catheter 352 with a lumen 354. Embolic coil system 350 also includes an embolic coil delivery wire 356 and an embolic coil 362 disposed within lumen 354. Embolic coil delivery wire 356 includes a peanut-shaped head 360, and embolic coil 362 includes arms 364 and 366 extending from it. Arms 364 and 366 are detachably engaged with head 360 of embolic coil delivery wire 356.

Figure 15B:
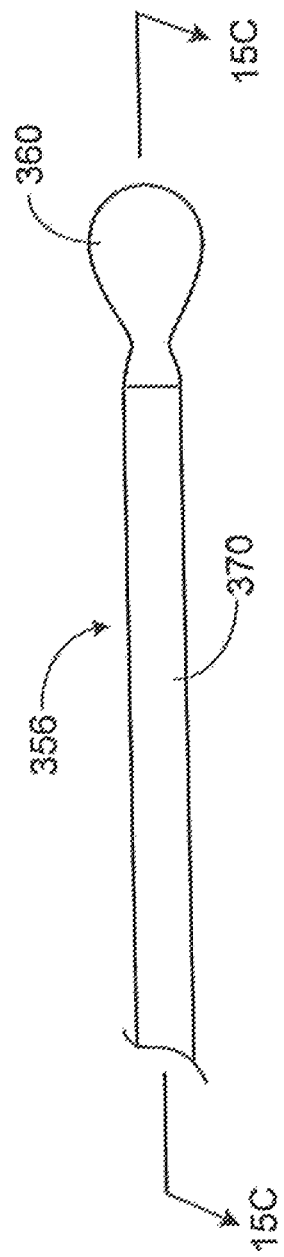
FIG. 15B is a side view of an embolic coil delivery wire of the embolic coil system of FIG. 15A.
Figure 15C:
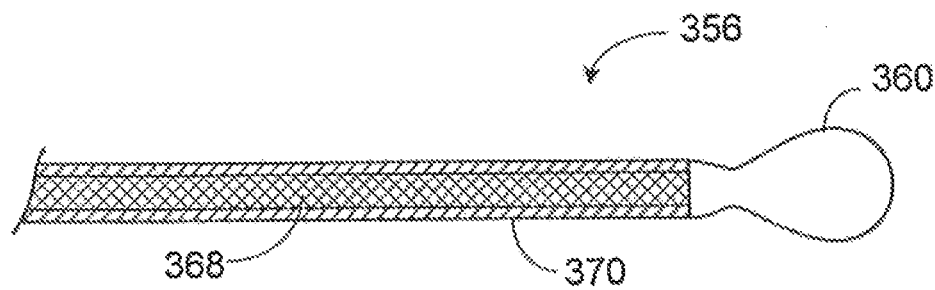
FIG. 15C is a cross-sectional view of the embolic coil delivery wire of FIG. 15B, taken along line 15C-15C.

FIGS. 15B and 15C show enlarged views of embolic coil delivery wire 356. As shown in FIG. 15C, embolic coil delivery wire 356 includes a wire portion 368 surrounded by a sheath 370. Wire portion 368 is connected to head 360. However, in some embodiments, a wire portion can be integrally formed with a non-hook-shaped head.

Figure 15D:
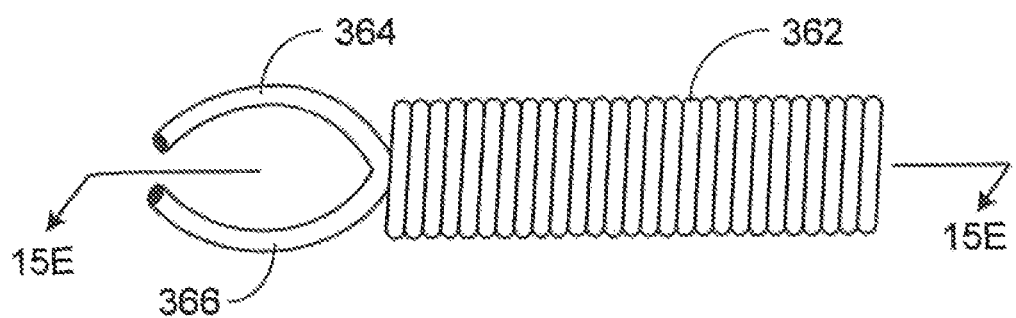
FIG. 15D is a side view of an embolic coil from the embolic coil system of FIG. 15A.
Figure 15E:
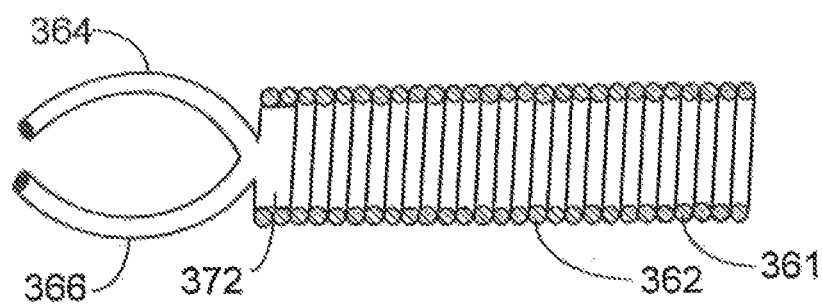
FIG. 15E is a cross-sectional view of the embolic coil of FIG. 15D, taken along line 15E-15E.

FIGS. 15D and 15E show enlarged views of embolic coil 362. As shown in FIG. 15E, arms 364 and 366 are integrally formed with an attachment portion 372 that is attached to embolic coil body 361 of embolic coil 362.

As another example, while embolic coils and embolic coil delivery wires with two arms extending from them have been described, in some embodiments, more than two arms (e.g., three arms, four arms, five arms, 10 arms, 16 arms) can extend from an embolic coil or an embolic coil delivery wire.

As a further example, while embolic coils and embolic coil delivery wires with peanut-shaped heads have been described, in some embodiments, an embolic coil or an embolic coil delivery wire can have a head that is not peanut-shaped. For example, in certain embodiments, an embolic coil or an embolic coil delivery wire can have a conical head.

As an additional example, while embolic coils and embolic coil delivery wires with heads that are rotationally symmetric about a longitudinal axis have been described, in some embodiments, an embolic coil or an embolic coil delivery wire can have a head that is not rotationally symmetric about a longitudinal axis. In certain embodiments, an embolic coil or an embolic coil delivery wire can have a head that is not rotationally symmetric about any axis.

As another example, in some embodiments, an embolic coil or an embolic coil delivery wire can have a head including a lumen. This can, for example, allow fluids (e.g., contrast agent, saline solution) to flow through the head during delivery and/or use of the embolic coil or embolic coil delivery wire.

Figure 16:
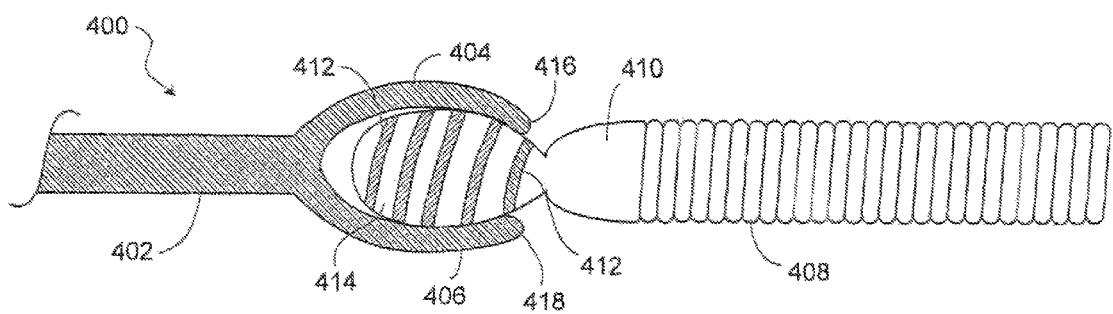
FIG. 16 is a side view of an embodiment of an embolic coil system.

As an additional example, in certain embodiments, an embolic coil or an embolic coil delivery wire can include a head having one or more grooves in it. For example, FIG. 16 shows an embolic coil system 400 including an embolic coil delivery wire 402 with arms 404 and 406 extending from it, and an embolic coil 408 having a head 410. Head 410 includes a helical groove 412 on its surface 414. The tip 416 of arm 404 and the tip 418 of arm 406 each are disposed within groove 412. The presence of groove 412 on head 410 can, for example, enhance the engagement of arms 404 and 406 with head 410.

Figure 17:
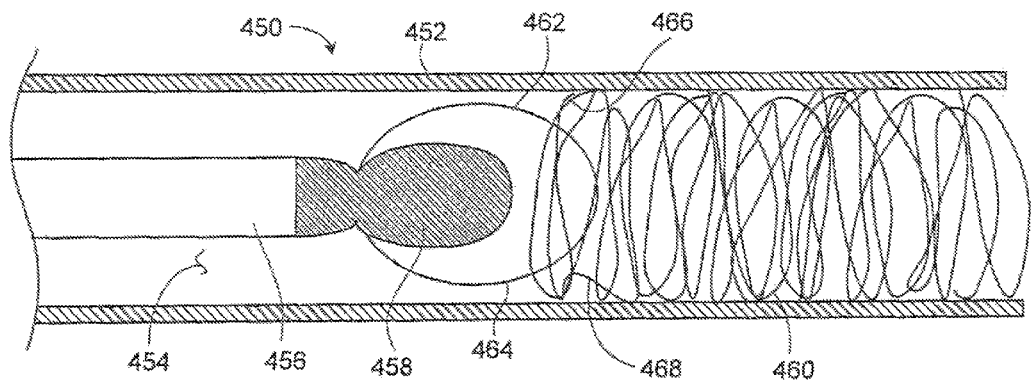
FIG. 17 is a side view in partial cross-section of an embodiment of an embolic coil system.

As a further example, in some embodiments, an embolic coil can include an embolic coil body and one or more arms that are integrally formed with the embolic coil body. For example, FIG. 17 shows an embolic coil system 450 including a catheter 452 having a lumen 454, an embolic coil delivery wire 456 having a head 458, and an embolic coil 460 including two arms 462 and 464 that are detachably engaged with head 458. Embolic coil 460 is formed of two coiled wires 466 and 468 that are co-wound with each other. Arm 462 is formed from an end of coiled wire 466, and arm 464 is formed from an end of coiled wire 468.

As another example, while arms have been described as being used to engage an embolic coil with an embolic coil delivery wire, in certain embodiments, one or more other devices can be used to engage an embolic coil with an embolic coil delivery wire. For example, FIG. 18A shows an embolic coil system 500 including a catheter 501 having a lumen 502, and an embolic coil delivery wire 504 and an embolic coil 506 disposed in lumen 502. Embolic coil delivery wire 504 has a tubular mesh member 508 in its distal section 510. Tubular mesh member 508 is engaged with a head 512 of an embolic coil 506. Catheter 501 helps to restrain tubular mesh member 508. As shown in FIG. 18B, when embolic coil delivery wire 504 is pushed in the direction of arrow A4, tubular mesh member 508 exits catheter 501 and opens up. As shown in FIG. 18C, when tubular mesh member 508 has opened up sufficiently, tubular mesh member 508 releases embolic coil 506. Tubular mesh member 508 can be formed of, for example, one or more metals (e.g., platinum) and/or metal alloys (e.g., stainless steel, cobalt-chromium alloys such as Elgiloy®). In certain embodiments, tubular mesh member 508 can be formed of tantalum-cored wire. This can, for example, result in tubular mesh member 508 being sufficiently radiopaque to be viewed using X-ray fluoroscopy.

In some embodiments, an embolic coil delivery wire including a tubular mesh member can be disposed within a lumen of a sheath that, in turn, is disposed within a lumen of a catheter. The embolic coil delivery wire can be used to deliver an embolic coil by pushing the embolic coil delivery wire distally and withdrawing the sheath proximally, thereby exposing the tubular mesh member and releasing the embolic coil.

In certain embodiments, an embolic coil delivery wire can include a tubular mesh member that is engaged with an embolic coil (e.g., a head of an embolic coil), and when the tubular mesh member and the embolic coil are unconstrained by a delivery device, the tubular mesh member can have a retention strength that is less than the flexural spring strength of the embolic coil. The result can be that the tubular mesh member disengages from the embolic coil, thereby deploying the embolic coil.

As an additional example, in certain embodiments, an embolic coil can include fibers. For example, FIG. 19 shows embolic coil 600 including a peanut-shaped head 602, an embolic coil body 604, and fibers 606 tightly fitted between consecutive windings (e.g., windings 608 and 610) of embolic coil body 604. In some embodiments in which an embolic coil includes fibers, the occlusion of a target site by the embolic coil can be accelerated by the fibers, which can enhance thrombosis at the target site. An accelerated embolization procedure can benefit the subject by, for example, reducing exposure time to fluoroscopy.

Fibers 606 typically can be made of one or more materials that can enhance thrombosis (e.g., at a target site). In some embodiments, fibers 606 can be made of one or more polyesters and/or polyamides. Examples of materials from which fibers 606 can be made include polyethylene terephthalate (e.g., Dacron®), nylon, and collagen. In certain embodiments, fibers 606 can have a length of from about 0.5 millimeter to about five millimeters (e.g., about 2.5 millimeters).

While FIG. 19 shows bunches of fibers 606 that are all separated from their neighboring bunches of fibers 606 by the same number of windings, in some embodiments, an embolic coil can have a different configuration of fibers. For examples, in certain embodiments, an embolic coil can have only one bunch of fibers, or can have bunches of fibers that are separated from their neighboring bunches of fibers by different numbers of windings. As an example, one bunch of fibers on an embolic coil may be separated from a neighboring bunch of fibers by three windings, while another bunch of fibers on the embolic coil is separated from a neighboring bunch of fibers by five windings.

In some embodiments, a fibered embolic coil such as embolic coil 600 can be formed as follows. After the embolic coil has been formed into its secondary shape, fibers can be attached to the embolic coil. In some embodiments, an embolic coil can be stretched prior to attaching fibers to the embolic coil, so that the embolic coil is in its extended primary shape, and can then be loaded onto a fibering mandrel (e.g., a fibering mandrel from Sematool Mold and Die Co., Santa Clara, Calif.). In certain embodiments, fibers can be snapped between windings of an embolic coil. In some embodiments, fibers can be tied to windings of an embolic coil and/or wrapped around windings of an embolic coil. In certain embodiments, fibers can be bonded (e.g., adhesive bonded) to windings of an embolic coil. In some embodiments, one portion (e.g., one end) of a bunch of fibers can be snapped in between windings in one region of an embolic coil, and another portion (e.g., the other end) of the same bunch of fibers can be wrapped around part of the embolic coil and snapped in between windings in another region of the embolic coil.

As a further example, in some embodiments, an embolic coil can have at least two regions (e.g., three, four, five, 10, 15, 20) with different outer diameters. Embolic coils including regions with different outer diameters are described, for example, in Elliott et al., U.S. Patent Application Publication No. US 2006/0116711 A1, published on Jun. 1, 2006, and entitled "Embolic Coils", and Buiser et al., U.S. patent application Ser. No. 11/430,602, filed on May 9, 2006, and entitled "Embolic Coils", both of which are incorporated herein by reference.

As another example, while embodiments have been shown in which the pitch of an embolic coil is substantially the same in different regions of the embolic coil, in certain embodiments, the pitch of an embolic coil can differ in different regions of the embolic coil. For example, some regions of an embolic coil can have a pitch of 0.002 inch, while other regions of an embolic coil can have a pitch of 0.004 inch.

As an additional example, in some embodiments, an embolic coil delivery wire can be temporarily attached to an embolic coil by one or more bioerodible connectors. For example, in certain embodiments, an embolic coil delivery wire can have one or more arms extending from it, and the arms can be connected to an embolic coil (e.g., a head of an embolic coil) by one or more bioerodible connectors.

Figure 20:
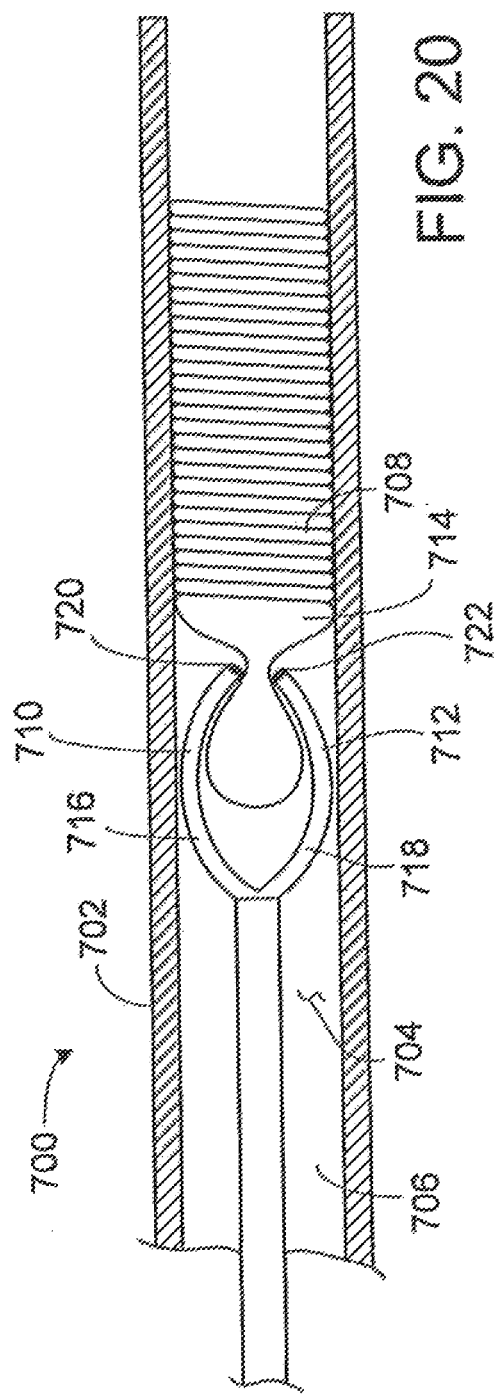
FIG. 20 is a side view in partial cross-section of an embodiment of an embolic coil system.

As a further example, in some embodiments, an embolic coil can be delivered to a target site by electrolytically detaching the embolic coil from an embolic coil delivery wire. For example, FIG. 20 shows an embolic coil system 700 including a catheter 702 having a lumen 704, and an embolic coil delivery wire 706 and an embolic coil 708 disposed in lumen 704. Embolic coil delivery wire 700 includes two arms 710 and 712 that are detachably engaged with a head 714 of embolic coil 708. Arms 710 and 712 include insulated portions 716 and 718, and metal portions 720 and 722 that are welded to head 714. Metal portions 720 and 722 are electrolytically detachable from head 714. Electrolytic detachment is described, for example, in Guglielmi et al., U.S. Pat. No. 5,893,385, which is incorporated herein by reference.

Figure 21:
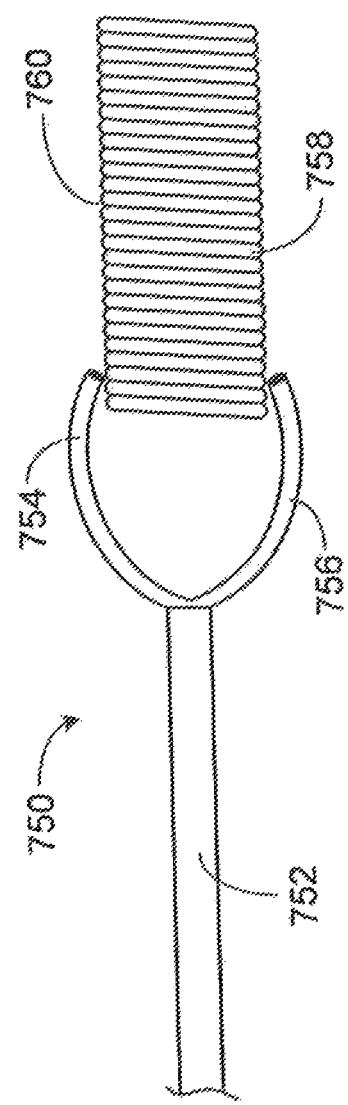
FIG. 21 is a side view of an embodiment of an embolic coil system.

As an additional example, in some embodiments, an embolic coil delivery wire can include arms that are connected directly to an embolic coil body of an embolic coil. For example, FIG. 21 shows an embolic coil system 750 including an embolic coil delivery wire 752 having arms 754 and 756, and an embolic coil 758 including an embolic coil body 760. Arms 754 and 756 are connected directly to embolic coil body 760. In certain embodiments, embolic coil 758 can be delivered to a target site by electrolytically detaching embolic coil body 760 from arms 754 and 756.

As another example, in some embodiments, multiple (e.g., two, three, four) embolic coils can be delivered using one delivery device.

As an additional example, in certain embodiments, a treatment site can be occluded by using embolic coils in conjunction with other occlusive devices. For example, embolic coils can be used with embolic particles such as those described in Buiser et al., U.S. Patent Application Publication No. US 2003/0185896 A1, published on Oct. 2, 2003, and entitled "Embolization", and in Lanphere et al., U.S. Patent Application Publication No. US 2004/0096652 A1, published on May 20, 2004, and entitled "Embolization", both of which are incorporated herein by reference. In some embodiments, embolic coils can be used in conjunction with one or more embolic gels. Embolic gels are described, for example, in Richard et al., U.S. Patent Application Publication No. US 2006/0045900 A1, published on Mar. 2, 2006, and entitled "Embolization", which is incorporated herein by reference.

Figure 22:
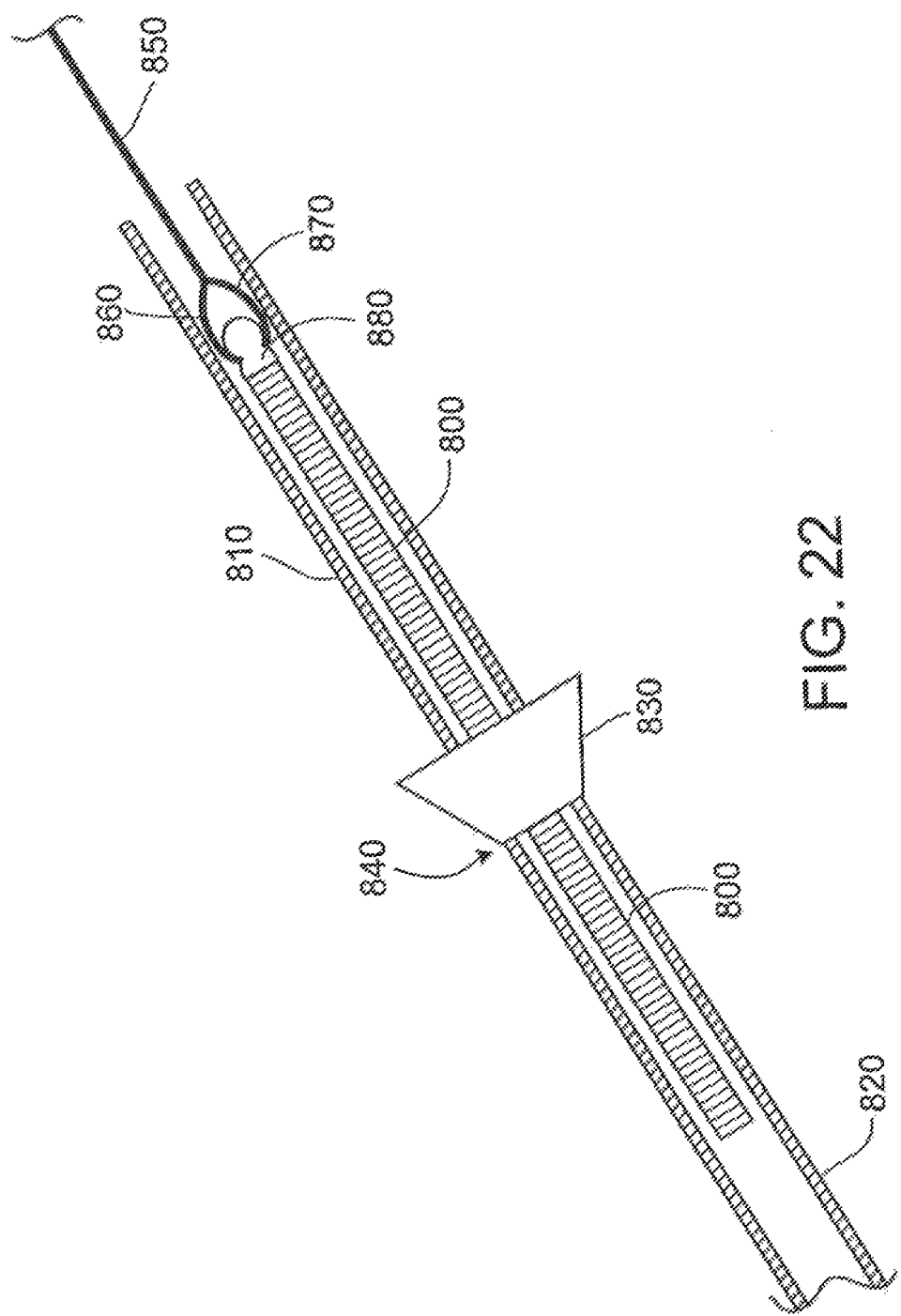
FIG. 22 illustrates the delivery of an embodiment of an embolic coil from an introducer sheath into a delivery device.

As another example, in certain embodiments, an embolic coil can be loaded into a delivery device using an introducer sheath. For example, FIG. 22 illustrates the transfer of an embolic coil 800 from an introducer sheath 810 into a catheter 820. A hub 830 located at the proximal end 840 of catheter 820 directs the placement of introducer sheath 810. After introducer sheath 810 has been placed in hub 830, an embolic coil delivery wire 850, having two arms 860 and 870 that are detachably engaged with a head 880 of embolic coil 800, is used to push embolic coil 800 out of introducer sheath 810 and into catheter 820.

As an additional example, in some embodiments, an embolic coil can include one or more radiopaque markers. The radiopaque markers can, for example, be attached to one or more windings of the embolic coil.

As a further example, in certain embodiments, an end of an embolic coil can be heated and melted to make the end rounder and/or more biocompatible (e.g., atraumatic).

As another example, in some embodiments, an embolic coil can be formed of windings of a ribbon. Embolic coils that are formed of windings of a ribbon are described, for example, in Buiser et al., U.S. patent application Ser. No. 11/430,602, filed on May 9, 2006, and entitled "Embolic Coils", which is incorporated herein by reference.

Other embodiments are in the claims.

What is claimed is:

1. A system for treating a patient, comprising:
   a catheter having a proximal end, a distal end, and a lumen extending from the proximal end to the distal end;
   a delivery wire slidably disposed within the lumen, the delivery wire having a proximal end and a distal end; and
   an embolic device having a proximal and a distal end, wherein
   (a) the distal end of the delivery wire includes a structure expandable between first and second positions relative to the distal end of the catheter,
   (b) the proximal end of the embolic device includes a head with a helical groove on the outer surface of the head configured for enhanced engagement with the structure,
   (c) the structure interfits with the head when in the first position, and
   (d) the structure assumes the second position when the distal end of the delivery wire is positioned distally to the lumen of the catheter.

2. The system of claim 1, wherein the head is peanut shaped.

3. The system of claim 1, wherein the structure includes a tubular mesh.

4. The system of claim 1, wherein the head is conical.

5. The system of claim 1, wherein the head is not rotationally symmetrical about a longitudinal axis.

6. The system of claim 1, wherein the head is not rotationally symmetrical about any axis.

7. The system of claim 1, wherein the head includes a radiopaque marker.

8. A method of treating a patient, comprising the steps of:
   providing a system for treating a patient according to claim 1;
   inserting, into a body lumen of a patient, a distal end of the catheter to a position where embolization is desired;
   retracting the catheter relative to the delivery wire so that the distal end of the delivery wire extends past the distal end of the catheter, thereby allowing the structure to assume the second position and disengage the head.

9. A system for treating a patient, comprising:
   a catheter having a proximal end, a distal end, and a lumen extending from the proximal end to the distal end;
   a delivery wire slidably disposed within the lumen, the delivery wire having a proximal end and a distal end; and
   an embolic device having a proximal end and a distal end, wherein
   (a) the distal end of the delivery wire includes a plurality of arms expandable between first and second configurations,
   (b) the proximal end of the embolic device includes a head with a helical groove on the outer surface of the head configured for enhanced engagement with the plurality of arms,
   (c) the arms form an interference fit with the head when in the first configuration, and
   (d) the arms assume the second configuration when the distal end of the delivery wire is positioned distally relative to the catheter lumen.

10. The system of claim 9, wherein the arms are configured to flex such that the delivery wire can be inserted into a catheter having an inner diameter of between 0.018 inches and 0.035 inches.

11. The system of claim 9, wherein the structure includes two, three, five, ten or sixteen arms.

12. A method of treating a patient, comprising the steps of:
   providing a system for treating a patient according to claim 9;
   inserting, into a body lumen of a patient, a distal end of the catheter to a position where embolization is desired; and
   retracting the catheter relative to the delivery wire so that the distal end of the delivery wire extends past the distal end of the catheter, thereby allowing the arms to assume the second configuration and disengage the head.

* * * * *